United States Patent
Yamaguchi et al.

(10) Patent No.: US 10,000,763 B2
(45) Date of Patent: Jun. 19, 2018

(54) METHOD FOR REGULATING EXPRESSION OF SPECIFIC PROTEIN USING CYTOKININ-RESPONSIVE TRANSCRIPTION FACTOR, ISOPRENOID-PRODUCING PLANT HAVING GENE ENCODING CYTOKININ-RESPONSIVE TRANSCRIPTION FACTOR INTRODUCED THEREIN, AND METHOD FOR PRODUCING POLYISOPRENOID USING SAID ISOPRENOID-PRODUCING PLANT

(71) Applicant: SUMITOMO RUBBER INDUSTRIES, LTD., Kobe-shi, Hyogo (JP)

(72) Inventors: Haruhiko Yamaguchi, Kobe (JP); Yukino Inoue, Kobe (JP); Satoshi Kuroda, Kobe (JP)

(73) Assignee: SUMITOMO RUBBER INDUSTRIES, LTD., Kobe-Shi, Hyogo (JP)

( * ) Notice: Subject to any disclaimer, the term of this patent is extended or adjusted under 35 U.S.C. 154(b) by 0 days. days.

(21) Appl. No.: 14/429,606

(22) PCT Filed: Oct. 1, 2013

(86) PCT No.: PCT/JP2013/076630
§ 371 (c)(1),
(2) Date: Mar. 19, 2015

(87) PCT Pub. No.: WO2014/054602
PCT Pub. Date: Apr. 10, 2014

(65) Prior Publication Data
US 2015/0337324 A1    Nov. 26, 2015

(30) Foreign Application Priority Data
Oct. 2, 2012 (JP) .................. 2012-220633

(51) Int. Cl.
*C12N 15/82* (2006.01)
*C12P 5/00* (2006.01)
*C12P 5/02* (2006.01)
*C07K 14/415* (2006.01)

(52) U.S. Cl.
CPC ........ *C12N 15/8243* (2013.01); *C07K 14/415* (2013.01); *C12P 5/007* (2013.01); *C12P 5/02* (2013.01)

(58) Field of Classification Search
None
See application file for complete search history.

(56) References Cited

FOREIGN PATENT DOCUMENTS

| JP | 2007-105032 A | 4/2007 |
|---|---|---|
| JP | 2007-130010 A | 5/2007 |
| JP | 2010-187589 A | 9/2010 |
| WO | WO 2008/037431 A1 | 4/2008 |
| WO | WO 2013/081116 A1 | 6/2013 |

OTHER PUBLICATIONS

Hass et al., 2004, The EMBO Journal 23: 3290-3302, with Supplementary Data.*
Chiang, 2011, PhD thesis, Dartmouth College, pp. 1-201, May 18, 2011.*
Bhargava et al., 2013, Plant Physiology 162: 272-294.*
Maniatis et al., 1982, Molecular Cloning: A Laboratory Manual, Cold Spring Harbor Laboratory, pp. 324-343 and 387-389.*
Guo et al., 2004, Proceedings of the National Academy of Sciences USA 101: 9205-9210.*
Thornton et al., 2000, Nature Structural Biology, structural genomic supplement, Nov. 2000: 991-994.*
Keskin et al., 2004, Protein Science 13: 1043-1055.*
Vranová et al., 2012, Molecular Plant 5: 318-333.*
Cheng et al., SpringerPlus (2016) 5:1853.*
Pang and Meyerowitz, 1987, Nature Biotechnology 5: 1177-1181.*
Koornneef and Meinke, 2010, The Plant Journal 61: 909-921.*
Venkatachalam et al., 2007, Functional Plant Science and Biotechnology 1: 1-17.*
Minorsky, 2009, Plant Physiology 151: 481-482.*
Cutcliffe et al., "CRFs form protein-protein interactions with each other and with members of the cytokinin signalling pathway in *Arabidopsis* via the CRF domain," Journal of Experimental Botany (2011), vol. 62, No. 14, pp. 4995-5002.
Botella-Pavia et al., "Regulation of carotenoid biosynthesis in plants: evidence for a key role of hydroxymethylbutenyl diphosphate reductase in controlling the supply of plastidial isoprenoid precursors," The Plant Journal (2004), vol. 40, pp. 188-199.
D'Agostino et al., "Characterization of the Response of the *Arabidopsis* Response Regulator Gene Family to Cytokinin," Plant Physiology (Dec. 2000), vol. 124, pp. 1706-1717.
Estevez et al., "1-Deoxy-D-xylulouse-5-phosphate Synthase, a Limiting Enzyme for Plastidic Isoprenoid biosynthesis in Plants," The Journal of Biological Chemistry (2001), vol. 276, No. 25, pp. 22901-22909.
Hao et al., "Laticifer Differentation in *Hevea brasiliensis*: Induction by Exogenous Jasmonic Acid and Linolenic Acid," Annals of Botany (2000), vol. 85, pp. 37-43.

(Continued)

*Primary Examiner* — Amjad Abraham
*Assistant Examiner* — Bratislav Stankovic
(74) *Attorney, Agent, or Firm* — Birch, Stewart, Kolasch & Birch, LLP

(57) ABSTRACT

The present invention provides a method for enhancing the overall pathway of polyisoprenoid biosynthesis. The present invention further provides an isoprenoid-producing plant having an overall enhanced pathway of polyisoprenoid biosynthesis, and a method of producing a polyisoprenoid using such an isoprenoid-producing plant. The present invention relates to a method of regulating by a cytokinin-responsive transcription factor the expression of at least one protein selected from the group consisting of hydroxymethylglutaryl-CoA reductase, isopentenyl diphosphate isomerase, cis-prenyltransferase, and small rubber particle protein.

2 Claims, 1 Drawing Sheet

(56) References Cited

OTHER PUBLICATIONS

Sakai et al., "*Arabidopsis* ARP1 and ARR2 response regulators operate as transcriptional activators," The Plant Journal (2000), vol. 24, No. 6, pp. 703-711.
Sakai et al., "ARR1, a Transcription Factor for Genes Immediatley Responsive to Cytokinins," Science (Nov. 16, 2001), vol. 294, pp. 1519-1521.
Seibutsu-kogaku (Bioengineering) (2011), vol. 89, pp. 649-652, with partial English translation.
Ruderman et al., "Mitochondrial/Cytosolic Acetyl CoA and Rubber Biosynthesis Genes Expression in Hevea Brasiliensis Latex and Rubber Yield," Kasetsart J. (Nat. Sci.), vol. 46, pp. 346-362 (2012).

* cited by examiner

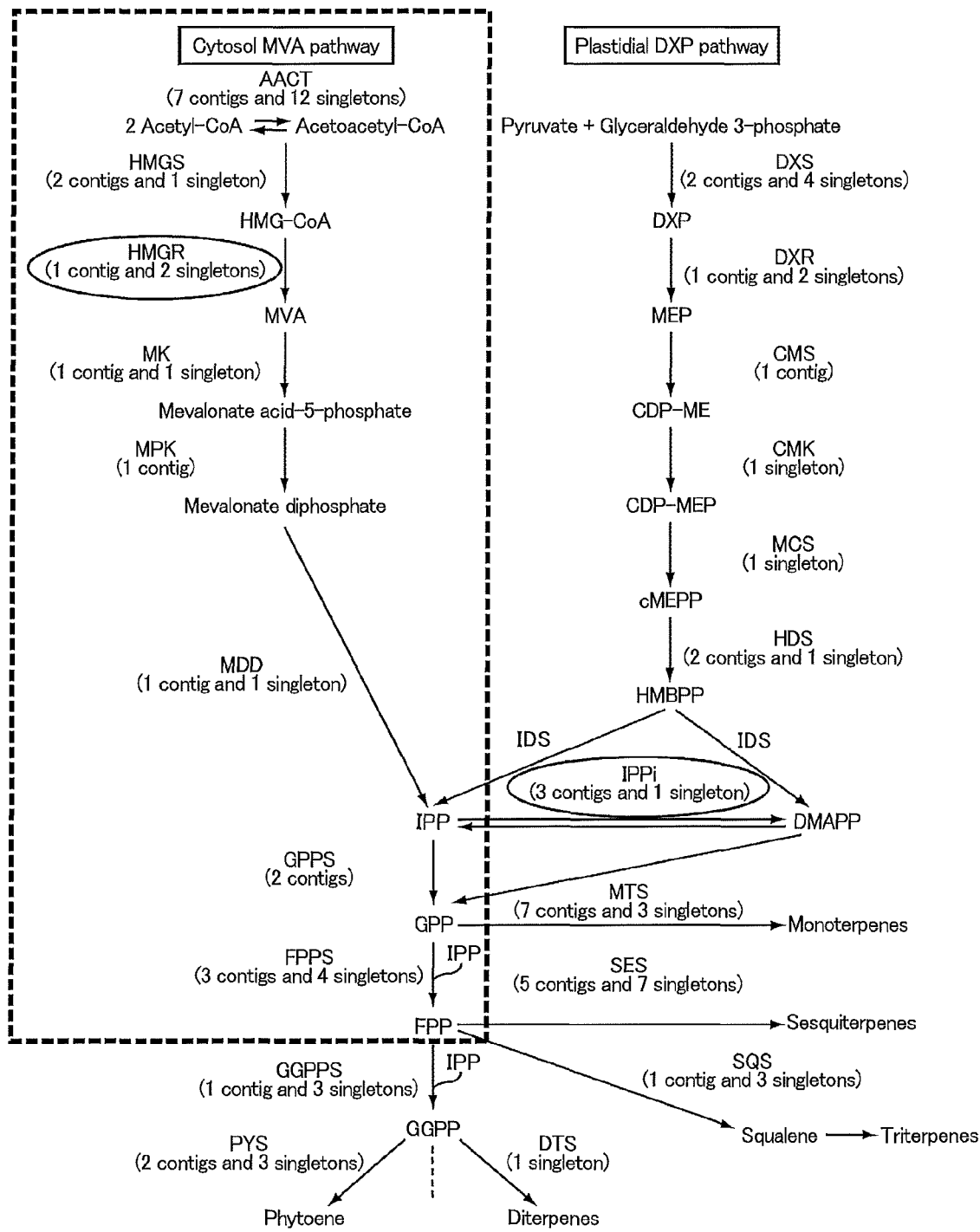

```
                         SEQUENCE LISTING

<160> NUMBER OF SEQ ID NOS: 24

<210> SEQ ID NO 1
<211> LENGTH: 2073
<212> TYPE: DNA
<213> ORGANISM: Arabidopsis thaliana

<400> SEQUENCE: 1
atgatgaatc cgagtcacgg aagaggactc ggatcggctg gtgggtccag ctccggtaga      60
aatcaaggag gtggtggtga daccgtcgtc gagatgtttc cttctggtct tcgagttctt     120
gtcgttgacg atgacccaac ttgtctcatg atcttagaga ggatgcttag gacttgtctt     180
tacgaagtaa cgaaatgcaa cagagcagag atggcattgt ctctgctccg gaagaacaaa     240
catggattcg atatagtaat cagtgatgtt catatgcctg acatggacgg tttcaagctt     300
cttgagcatg ttggtctaga gatggactta cctgttatca tgatgtctgc ggatgattca     360
aagagtgtgg ttctaaaggg agtaacgcac ggtgcggttg attaccttat caagcctgta     420
cgtatggagg cacttaagaa catatggcag catgtagtta ggaagaggag aagtgaatgg     480
agtgtaccgg aacattctgg gagcattgag gagactggcg agagacagca gcagcaacat     540
agaggaggtg gtggtggtgc agctgtttct ggtggagagg atgcggtgga tgataactca     600
tcctcggtta acgaaggtaa caattggagg agcagttcac ggaagaggaa agacgaggaa     660
ggagaagagc aaggagatga taaggacgaa gatgcgtcga atttgaagaa accgcgtgtc     720
gtctggtctg ttgaattgca tcagcagttt gttgctgctg ttaatcagct cggcgttgag     780
aaggcggttc ctaaaaagat cttagagctg atgaatgttc ctggtctaac ccgagaaaac     840
gtagcaagtc acctccagaa ataccggata tatctaagac ggcttggagg ggtatcgcag     900
```

```
caccaaggca atcttaacaa ctcgtttatg acgggtcagg atgcgagctt cggacctctt    960
tcgacattga atgggtttga tcttcaagca ctagccgtca caggtcagtt acctgcacag   1020
agtcttgcac agcttcaagc cgctggttta ggccggcctg cgatggtctc taagtcaggt   1080
ttgccggttt cctccattgt ggatgagaga agcatcttca gctttgacaa cacgaaaaca   1140
agatttggag aagggcttgg gcatcacggg caacaacccc aacagcaacc acagatgaac   1200
ttacttcacg gtgtccccac gggtttacaa cagcagcttc ctatgggtaa tcgaatgagt   1260
attcaacaac agattgctgc tgttcgagct ggaaatagtg ttcaaaacaa cggaatgctg   1320
atgcctctag cgggtcagca gtcttttgcct cggggaccac cgcctatgct aacctcttcg   1380
caatcatcca tcaggcagcc gatgttatca accgcatttt ccgagagaag tggtttctct   1440
ggaaggaaca atatccccga gagcagcaga gtgttaccga caagttacac taatctcaca   1500
acacaacact catcaagctc gatgccttat aacaacttcc aaccagaact tcccgtgaac   1560
agtttcccgc tggcaagtgc accagggata tcagtaccgg ttcggaaagc cacttcttac   1620
caggaagagg ttaacagctc cgaagcgggt ttcactacgc cgagctacga catgttcacc   1680
accagacaga atgattggga tctgaggaat attggaatag cctttgactc acatcaggac   1740
tcagaatccg ctgcgttttc cgcttcagaa gcctactctt cttcgtccat gtcaagacac   1800
aacacgacag ttgcagccac cgagcatggc cgaaaccacc agcagccacc atcgggaatg   1860
gtacagcacc atcaggttta tgcagacgga aacggtggtt cagtgagggt gaaatcagag   1920
agagtggcta cggatacagc aacaatggcg tttcacgagc agtatagtaa tcaagaagat   1980
cttatgagcg cacttcttaa gcaggaaggg attgcaccgg ttgatggcga attcgacttt   2040
gacgcatact ccatcgataa cattccggtt tga                               2073

<210> SEQ ID NO 2
<211> LENGTH: 690
<212> TYPE: PRT
<213> ORGANISM: Arabidopsis thaliana

<400> SEQUENCE: 2

Met Met Asn Pro Ser His Gly Arg Gly Leu Gly Ser Ala Gly Gly Ser
1               5                   10                  15

Ser Ser Gly Arg Asn Gln Gly Gly Gly Glu Thr Val Val Glu Met
            20                  25                  30

Phe Pro Ser Gly Leu Arg Val Leu Val Asp Asp Pro Thr Cys
        35                  40                  45

Leu Met Ile Leu Glu Arg Met Leu Arg Thr Cys Leu Tyr Glu Val Thr
50                  55                  60

Lys Cys Asn Arg Ala Glu Met Ala Leu Ser Leu Leu Arg Lys Asn Lys
65                  70                  75                  80

His Gly Phe Asp Ile Val Ile Ser Asp Val His Met Pro Asp Met Asp
                85                  90                  95

Gly Phe Lys Leu Leu Glu His Val Gly Leu Glu Met Asp Leu Pro Val
            100                 105                 110

Ile Met Met Ser Ala Asp Asp Ser Lys Ser Val Val Leu Lys Gly Val
        115                 120                 125

Thr His Gly Ala Val Asp Tyr Leu Ile Lys Pro Val Arg Met Glu Ala
    130                 135                 140

Leu Lys Asn Ile Trp Gln His Val Val Arg Lys Arg Ser Glu Trp
145                 150                 155                 160
```

```
Ser Val Pro Glu His Ser Gly Ser Ile Glu Glu Thr Gly Glu Arg Gln
                165                 170                 175
Gln Gln Gln His Arg Gly Gly Gly Gly Ala Ala Val Ser Gly Gly
        180                 185                 190
Glu Asp Ala Val Asp Asp Asn Ser Ser Val Asn Glu Gly Asn Asn
        195                 200                 205
Trp Arg Ser Ser Arg Lys Arg Lys Asp Glu Glu Gly Glu Glu Gln
    210                 215                 220
Gly Asp Asp Lys Asp Glu Asp Ala Ser Asn Leu Lys Lys Pro Arg Val
225                 230                 235                 240
Val Trp Ser Val Glu Leu His Gln Gln Phe Val Ala Ala Val Asn Gln
                245                 250                 255
Leu Gly Val Glu Lys Ala Val Pro Lys Lys Ile Leu Glu Leu Met Asn
                260                 265                 270
Val Pro Gly Leu Thr Arg Glu Asn Val Ala Ser His Leu Gln Lys Tyr
                275                 280                 285
Arg Ile Tyr Leu Arg Arg Leu Gly Gly Val Ser Gln His Gln Gly Asn
    290                 295                 300
Leu Asn Asn Ser Phe Met Thr Gly Gln Asp Ala Ser Phe Gly Pro Leu
305                 310                 315                 320
Ser Thr Leu Asn Gly Phe Asp Leu Gln Ala Leu Ala Val Thr Gly Gln
                325                 330                 335
Leu Pro Ala Gln Ser Leu Ala Gln Leu Gln Ala Ala Gly Leu Gly Arg
                340                 345                 350
Pro Ala Met Val Ser Lys Ser Gly Leu Pro Val Ser Ser Ile Val Asp
                355                 360                 365
Glu Arg Ser Ile Phe Ser Phe Asp Asn Thr Lys Thr Arg Phe Gly Glu
    370                 375                 380
Gly Leu Gly His His Gly Gln Gln Pro Gln Gln Pro Gln Met Asn
385                 390                 395                 400
Leu Leu His Gly Val Pro Thr Gly Leu Gln Gln Gln Leu Pro Met Gly
                405                 410                 415
Asn Arg Met Ser Ile Gln Gln Gln Ile Ala Ala Val Arg Ala Gly Asn
                420                 425                 430
Ser Val Gln Asn Asn Gly Met Leu Met Pro Leu Ala Gly Gln Gln Ser
                435                 440                 445
Leu Pro Arg Gly Pro Pro Met Leu Thr Ser Ser Gln Ser Ser Ile
    450                 455                 460
Arg Gln Pro Met Leu Ser Asn Arg Ile Ser Glu Arg Ser Gly Phe Ser
465                 470                 475                 480
Gly Arg Asn Asn Ile Pro Glu Ser Ser Arg Val Leu Pro Thr Ser Tyr
                485                 490                 495
Thr Asn Leu Thr Thr Gln His Ser Ser Ser Met Pro Tyr Asn Asn
                500                 505                 510
Phe Gln Pro Glu Leu Pro Val Asn Ser Phe Pro Leu Ala Ser Ala Pro
                515                 520                 525
Gly Ile Ser Val Pro Val Arg Lys Ala Thr Ser Tyr Gln Glu Glu Val
                530                 535                 540
Asn Ser Ser Glu Ala Gly Phe Thr Thr Pro Ser Tyr Asp Met Phe Thr
545                 550                 555                 560
Thr Arg Gln Asn Asp Trp Asp Leu Arg Asn Ile Gly Ile Ala Phe Asp
                565                 570                 575
Ser His Gln Asp Ser Glu Ser Ala Ala Phe Ser Ala Ser Glu Ala Tyr
```

```
            580             585             590
Ser Ser Ser Ser Met Ser Arg His Asn Thr Thr Val Ala Ala Thr Glu
            595             600             605

His Gly Arg Asn His Gln Gln Pro Pro Ser Gly Met Val Gln His His
            610             615             620

Gln Val Tyr Ala Asp Gly Asn Gly Gly Ser Val Arg Val Lys Ser Glu
625             630             635             640

Arg Val Ala Thr Asp Thr Ala Thr Met Ala Phe His Glu Gln Tyr Ser
                645             650             655

Asn Gln Glu Asp Leu Met Ser Ala Leu Leu Lys Gln Glu Gly Ile Ala
            660             665             670

Pro Val Asp Gly Glu Phe Asp Phe Asp Ala Tyr Ser Ile Asp Asn Ile
            675             680             685

Pro Val
    690

<210> SEQ ID NO 3
<211> LENGTH: 1995
<212> TYPE: DNA
<213> ORGANISM: Arabidopsis thaliana

<400> SEQUENCE: 3
atggtaaatc cgggtcacgg aagaggaccc gattcgggta ctgctgctgg tgggtcaaac      60
tccgacccgt ttcctgcgaa tcttcgagtt cttgtcgttg atgatgatcc aacttgtctc     120
atgatcttag agaggatgct tatgacttgt ctctacagag taactaaatg taacagagca     180
gagagcgcat tgtctctgct tcggaagaac aagaatggtt ttgatattgt cattagtgat     240
gttcatatgc ctgacatgga tggtttcaag ctccttgaac acgttggttt agagatggat     300
ttacctgtta tcatgatgtc tgcggatgat tcgaagagcg ttgtgttgaa aggagtgact     360
cacggtgcag ttgattacct catcaaaccg gtacgtattg aggctttgaa gaatatatgg     420
caacatgtgg tgcggaagaa gcgtaacgag tggaatgttt ctgaacattc tggaggaagt     480
attgaagata ctggcggtga cagggacagg cagcagcagc atagggagga tgctgataac     540
aactcgtctt cagttaatga agggaacggg aggagctcga ggaagcggaa ggaagaggaa     600
gtagatgatc aagggatgat aaggaagac tcatcgagtt aaagaaacc acgcgtggtt     660 tggtctgttg aattgcatca gcagtttgtt gctgctgtga atcagctagg cgttgacaaa     720
gctgttccta gaagatcttt agagatgatg aatgtacccg gctaacgcg agaaaacgta      780 gccagtcacc tccagaagta tcggatatat ctgagacggc ttggaggagt atcgcaacac     840
caaggaaata tgaaccattc gtttatgact ggtcaagatc agagttttgg acctctttct     900
tcgttgaatg gatttgatct tcaatcttta gctgttactg gtcagctccc tcctcagagc     960
cttgcacagc ttcaagcagc tggtcttggc cggcctacac tcgctaaacc agggatgtcg    1020
gtttctcccc ttgtagatca gagaagcatc ttcaactttg aaaacccaaa aataagattt    1080
ggagacggac atggtcagac gatgaacaat ggaaatttgc ttcatggtgt cccaacgggt    1140
agtcacatgc gtctgcgtcc tggacagaat gttcagagca gcggaatgat gttgccagta    1200
gcagaccagc tacctcgagg aggaccatcg atgctaccat ccctcgggca acagccgata    1260
ttgtcaagca gcgtttcaag aagaagcgat ctcactggtg cgctggcggt tagaaacagt    1320
atccccgaga ccaacagcag agtgttacca actactcact cggtcttcaa taacttcccc    1380
gcggatctac ctcgcagcag cttcccgttg caagtgccc cagggatttc agttccagta    1440
```

-continued

```
tcagtttctt accaagaaga ggtcaacagc tcggatgcaa aaggaggttc atcagctgct    1500
actgctggat ttggtaaccc aagctacgac atatttaacg attttccgca gcaccaacag    1560
cacaacaaga acatcagcaa taaactaaac gattgggatc tgcggaatat gggattggtc    1620
ttcagttcca atcaggacgc agcaactgca accgcaaccg cagcattttc cacttcggaa    1680
gcatactctt cgtcttctac gcagagaaaa agacgggaaa cggacgcaac agttgtgggt    1740
gagcatgggc agaacctgca gtcaccgagc cggaatctgt atcatctgaa ccacgttttt    1800
atggacggtg gttcagtcag agtgaagtca gaaagagtgg cggagacagt gacttgtcct    1860
ccagcaaata cattgtttca cgagcagtat aatcaagaag atctgatgag cgcatttctc    1920
aaacaggaag gcatcccatc cgtagataac gagttcgaat ttgacggata ctccatcgat    1980
aatatccagg tctga                                                    1995
```

<210> SEQ ID NO 4
<211> LENGTH: 664
<212> TYPE: PRT
<213> ORGANISM: Arabidopsis thaliana

<400> SEQUENCE: 4

```
Met Val Asn Pro Gly His Gly Arg Gly Pro Asp Ser Gly Thr Ala Ala
  1               5                  10                  15

Gly Gly Ser Asn Ser Asp Pro Phe Pro Ala Asn Leu Arg Val Leu Val
                 20                  25                  30

Val Asp Asp Asp Pro Thr Cys Leu Met Ile Leu Glu Arg Met Leu Met
             35                  40                  45

Thr Cys Leu Tyr Arg Val Thr Lys Cys Asn Arg Ala Glu Ser Ala Leu
         50                  55                  60

Ser Leu Leu Arg Lys Asn Lys Asn Gly Phe Asp Ile Val Ile Ser Asp
 65                  70                  75                  80

Val His Met Pro Asp Met Asp Gly Phe Lys Leu Leu Glu His Val Gly
                 85                  90                  95

Leu Glu Met Asp Leu Pro Val Ile Met Met Ser Ala Asp Asp Ser Lys
                100                 105                 110

Ser Val Val Leu Lys Gly Val Thr His Gly Ala Val Asp Tyr Leu Ile
            115                 120                 125

Lys Pro Val Arg Ile Glu Ala Leu Lys Asn Ile Trp Gln His Val Val
        130                 135                 140

Arg Lys Lys Arg Asn Glu Trp Asn Val Ser Glu His Ser Gly Gly Ser
145                 150                 155                 160

Ile Glu Asp Thr Gly Gly Asp Arg Asp Arg Gln Gln His Arg Glu
                165                 170                 175

Asp Ala Asp Asn Asn Ser Ser Val Asn Glu Gly Asn Gly Arg Ser
            180                 185                 190

Ser Arg Lys Arg Lys Glu Glu Glu Val Asp Asp Gln Gly Asp Asp Lys
        195                 200                 205

Glu Asp Ser Ser Ser Leu Lys Lys Pro Arg Val Val Trp Ser Val Glu
    210                 215                 220

Leu His Gln Gln Phe Val Ala Ala Val Asn Gln Leu Gly Val Asp Lys
225                 230                 235                 240

Ala Val Pro Lys Lys Ile Leu Glu Met Met Asn Val Pro Gly Leu Thr
                245                 250                 255

Arg Glu Asn Val Ala Ser His Leu Gln Lys Tyr Arg Ile Tyr Leu Arg
            260                 265                 270
```

Arg Leu Gly Gly Val Ser Gln His Gln Gly Asn Met Asn His Ser Phe
                275                 280                 285

Met Thr Gly Gln Asp Gln Ser Phe Gly Pro Leu Ser Ser Leu Asn Gly
            290                 295                 300

Phe Asp Leu Gln Ser Leu Ala Val Thr Gly Gln Leu Pro Pro Gln Ser
305                 310                 315                 320

Leu Ala Gln Leu Gln Ala Ala Gly Leu Gly Arg Pro Thr Leu Ala Lys
                325                 330                 335

Pro Gly Met Ser Val Ser Pro Leu Val Asp Gln Arg Ser Ile Phe Asn
            340                 345                 350

Phe Glu Asn Pro Lys Ile Arg Phe Gly Asp Gly His Gly Gln Thr Met
        355                 360                 365

Asn Asn Gly Asn Leu Leu His Gly Val Pro Thr Gly Ser His Met Arg
370                 375                 380

Leu Arg Pro Gly Gln Asn Val Gln Ser Ser Gly Met Met Leu Pro Val
385                 390                 395                 400

Ala Asp Gln Leu Pro Arg Gly Gly Pro Ser Met Leu Pro Ser Leu Gly
                405                 410                 415

Gln Gln Pro Ile Leu Ser Ser Ser Val Ser Arg Arg Ser Asp Leu Thr
            420                 425                 430

Gly Ala Leu Ala Val Arg Asn Ser Ile Pro Glu Thr Asn Ser Arg Val
        435                 440                 445

Leu Pro Thr Thr His Ser Val Phe Asn Asn Phe Pro Ala Asp Leu Pro
450                 455                 460

Arg Ser Ser Phe Pro Leu Ala Ser Ala Pro Gly Ile Ser Val Pro Val
465                 470                 475                 480

Ser Val Ser Tyr Gln Glu Glu Val Asn Ser Ser Asp Ala Lys Gly Gly
                485                 490                 495

Ser Ser Ala Ala Thr Ala Gly Phe Gly Asn Pro Ser Tyr Asp Ile Phe
            500                 505                 510

Asn Asp Phe Pro Gln His Gln Gln His Asn Lys Asn Ile Ser Asn Lys
        515                 520                 525

Leu Asn Asp Trp Asp Leu Arg Asn Met Gly Leu Val Phe Ser Ser Asn
530                 535                 540

Gln Asp Ala Ala Thr Ala Thr Ala Thr Ala Ala Phe Ser Thr Ser Glu
545                 550                 555                 560

Ala Tyr Ser Ser Ser Ser Thr Gln Arg Lys Arg Arg Glu Thr Asp Ala
                565                 570                 575

Thr Val Val Gly Glu His Gly Asn Leu Gln Ser Pro Ser Arg Asn
            580                 585                 590

Leu Tyr His Leu Asn His Val Phe Met Asp Gly Gly Ser Val Arg Val
        595                 600                 605

Lys Ser Glu Arg Val Ala Glu Thr Val Thr Cys Pro Pro Ala Asn Thr
610                 615                 620

Leu Phe His Glu Gln Tyr Asn Gln Glu Asp Leu Met Ser Ala Phe Leu
625                 630                 635                 640

Lys Gln Glu Gly Ile Pro Ser Val Asp Asn Glu Phe Glu Phe Asp Gly
                645                 650                 655

Tyr Ser Ile Asp Asn Ile Gln Val
            660

<210> SEQ ID NO 5
<211> LENGTH: 1791
<212> TYPE: DNA

<213> ORGANISM: Arabidopsis thaliana

<400> SEQUENCE: 5

| | |
|---|---|
| atgactgttg aacaaaattt agaagctttg atcagtttc ctgtaggaat gagagttctt | 60 |
| gctgttgatg atgaccaaac ttgtctcaaa atccttgaat ctctccttcg tcactgccaa | 120 |
| taccatgtaa caacgacgaa ccaagcacaa aaggctttag agttattgag agagaacaag | 180 |
| aacaagtttg atctggttat tagtgatgtt gacatgcctg acatggatgg tttcaaactc | 240 |
| cttgagcttg ttggtcttga atggaccta cctgtcataa tgttgtctgc gcatagtgat | 300 |
| ccaaagtatg tgatgaaggg agttactcat ggtgcttgtg attatctact gaagccggtt | 360 |
| cgtattgagg agttgaagaa catatggcaa catgtcgtga aagtagatt tgataagaac | 420 |
| cgtgggagta ataataatgg tgataagaga atggatcag gtaatgaagg tgttgggaat | 480 |
| tctgatcaga acaatgggaa aggtaataga aaacgtaaag atcagtataa tgaagatgag | 540 |
| gatgaggata gagatgataa tgatgattcg tgtgctcaaa agaagcaacg tgttgtttgg | 600 |
| actgttgagc tgcataagaa atttgttgca gctgttaacc aattgggata tgagaaggct | 660 |
| atgcctaaaa agattttgga tctgatgaat gttgagaagc tcactagaga aaatgtggcc | 720 |
| agtcatcttc agaaattccg cctttacttg aagaggatca gtggtgtggc taatcagcaa | 780 |
| gctattatgg caaactctga gttacatttt atgcaaatga atggacttga tggtttccat | 840 |
| caccgcccaa tccctgttgg atctggtcag taccatggtg gggctcctgc aatgagatct | 900 |
| ttccctccaa acgggattct tggcagactc aatactcctt cggggatcgg tgtccgcagc | 960 |
| ctttcttctc ctcctgcagg aatgttcttg caaaaccaga ccgatatcgg aaagtttcac | 1020 |
| catgtctcat cacttcctct taaccacagt gatggaggaa acatacttca agggttgcca | 1080 |
| atgcctttag agttcgacca gcttcagaca acaacaaca aaagtagaaa catgaacagt | 1140 |
| aacaagagca ttgctgggac tccatggct tttcctagct tctctacgca acaaaactcg | 1200 |
| ctcatcagtg ctcctaataa caatgtcgtg gttctagaag gtcacccaca agcaactcct | 1260 |
| ccaggcttcc caggacacca gatcaataaa cgtttggagc attggtcaaa tgctgtatcc | 1320 |
| tcttcgactc accctcctcc cccggcacat aacagtaata gtatcaatca tcagttcgat | 1380 |
| gtctctccat taccgcattc tagacccgac cccttggaat ggaacaatgt gtcatcaagc | 1440 |
| tactctatac cattcgtga ctctgccaat acattgagtt ctccagcctt ggatacaaca | 1500 |
| aatccccgag ctttctgtag aaacacggac ttcgattcaa acacaaatgt gcaacctgga | 1560 |
| gtcttttatg gtccatccac ggatgctatg gctctgttga gtagtagtaa cccgaaagaa | 1620 |
| gggttcgtcg taggccaaca gaagttacag agtggtggat tcatggttgc agatgctggt | 1680 |
| tccttagatg atatagtcaa ctccacgatg aagcaggaac agagccaggg agatttgtct | 1740 |
| ggaggagatt tgggatatgg agggtttagt tcactcagaa catgcatatg a | 1791 |

<210> SEQ ID NO 6
<211> LENGTH: 596
<212> TYPE: PRT
<213> ORGANISM: Arabidopsis thaliana

<400> SEQUENCE: 6

Met Thr Val Glu Gln Asn Leu Glu Ala Leu Asp Gln Phe Pro Val Gly
1               5                   10                  15

Met Arg Val Leu Ala Val Asp Asp Gln Thr Cys Leu Lys Ile Leu
            20                  25                  30

Glu Ser Leu Leu Arg His Cys Gln Tyr His Val Thr Thr Thr Asn Gln

-continued

```
                35                  40                  45
Ala Gln Lys Ala Leu Glu Leu Leu Arg Glu Asn Lys Asn Lys Phe Asp
             50                  55                  60
Leu Val Ile Ser Asp Val Asp Met Pro Asp Met Asp Gly Phe Lys Leu
 65                  70                  75                  80
Leu Glu Leu Val Gly Leu Glu Met Asp Leu Pro Val Ile Met Leu Ser
                 85                  90                  95
Ala His Ser Asp Pro Lys Tyr Val Met Lys Gly Val Thr His Gly Ala
                100                 105                 110
Cys Asp Tyr Leu Leu Lys Pro Val Arg Ile Glu Glu Leu Lys Asn Ile
            115                 120                 125
Trp Gln His Val Val Arg Ser Arg Phe Asp Lys Asn Arg Gly Ser Asn
        130                 135                 140
Asn Asn Gly Asp Lys Arg Asp Gly Ser Gly Asn Glu Gly Val Gly Asn
145                 150                 155                 160
Ser Asp Gln Asn Asn Gly Lys Gly Asn Arg Lys Arg Lys Asp Gln Tyr
                165                 170                 175
Asn Glu Asp Glu Asp Glu Asp Arg Asp Asp Asn Asp Asp Ser Cys Ala
            180                 185                 190
Gln Lys Lys Gln Arg Val Val Trp Thr Val Glu Leu His Lys Lys Phe
        195                 200                 205
Val Ala Ala Val Asn Gln Leu Gly Tyr Glu Lys Ala Met Pro Lys Lys
210                 215                 220
Ile Leu Asp Leu Met Asn Val Glu Lys Leu Thr Arg Glu Asn Val Ala
225                 230                 235                 240
Ser His Leu Gln Lys Phe Arg Leu Tyr Leu Lys Arg Ile Ser Gly Val
                245                 250                 255
Ala Asn Gln Gln Ala Ile Met Ala Asn Ser Glu Leu His Phe Met Gln
            260                 265                 270
Met Asn Gly Leu Asp Gly Phe His His Arg Pro Ile Pro Val Gly Ser
        275                 280                 285
Gly Gln Tyr His Gly Gly Ala Pro Ala Met Arg Ser Phe Pro Pro Asn
        290                 295                 300
Gly Ile Leu Gly Arg Leu Asn Thr Pro Ser Gly Ile Gly Val Arg Ser
305                 310                 315                 320
Leu Ser Ser Pro Pro Ala Gly Met Phe Leu Gln Asn Gln Thr Asp Ile
                325                 330                 335
Gly Lys Phe His His Val Ser Ser Leu Pro Leu Asn His Ser Asp Gly
            340                 345                 350
Gly Asn Ile Leu Gln Gly Leu Pro Met Pro Leu Glu Phe Asp Gln Leu
        355                 360                 365
Gln Thr Asn Asn Lys Ser Arg Asn Met Asn Ser Asn Lys Ser Ile
        370                 375                 380
Ala Gly Thr Ser Met Ala Phe Pro Ser Phe Ser Thr Gln Gln Asn Ser
385                 390                 395                 400
Leu Ile Ser Ala Pro Asn Asn Val Val Val Leu Glu Gly His Pro
                405                 410                 415
Gln Ala Thr Pro Pro Gly Phe Pro Gly His Gln Ile Asn Lys Arg Leu
            420                 425                 430
Glu His Trp Ser Asn Ala Val Ser Ser Thr His Pro Pro Pro
        435                 440                 445
Ala His Asn Ser Asn Ser Ile Asn His Gln Phe Asp Val Ser Pro Leu
        450                 455                 460
```

Pro His Ser Arg Pro Asp Pro Leu Glu Trp Asn Asn Val Ser Ser
465                 470                 475                 480

Tyr Ser Ile Pro Phe Cys Asp Ser Ala Asn Thr Leu Ser Ser Pro Ala
                485                 490                 495

Leu Asp Thr Thr Asn Pro Arg Ala Phe Cys Arg Asn Thr Asp Phe Asp
            500                 505                 510

Ser Asn Thr Asn Val Gln Pro Gly Val Phe Tyr Gly Pro Ser Thr Asp
        515                 520                 525

Ala Met Ala Leu Leu Ser Ser Ser Asn Pro Lys Glu Gly Phe Val Val
    530                 535                 540

Gly Gln Gln Lys Leu Gln Ser Gly Gly Phe Met Val Ala Asp Ala Gly
545                 550                 555                 560

Ser Leu Asp Asp Ile Val Asn Ser Thr Met Lys Gln Glu Gln Ser Gln
                565                 570                 575

Gly Asp Leu Ser Gly Gly Asp Leu Gly Tyr Gly Gly Phe Ser Ser Leu
            580                 585                 590

Arg Thr Cys Ile
        595

<210> SEQ ID NO 7
<211> LENGTH: 873
<212> TYPE: DNA
<213> ORGANISM: Hevea brasiliensis

<400> SEQUENCE: 7
atgaaattat acaccggtga gaggccaagt gtgttcagac ttttagggaa gtatatgaga      60
aaagggttat atggcatcct aacccagggt cccatcccta ctcatcttgc cttcatattg     120
gatggaaaca ggaggtttgc taagaagcat aaactgccag aaggaggtgg tcataaggct     180
ggatttttag ctcttctgaa cgtgctaact tattgctatg agttaggagt gaaatatgcg     240
actatctatg cctttagcat cgataatttt cgaaggaaac tcatgaggt tcagtacgta      300 atgaatctaa tgctggagaa gattgaaggg atgatcatgg aagaagtat catcaatgca      360 tatgatattt gcgtacgttt tgtgggtaac ctgaagcttt taagtgagcc agtcaagacc     420
gcagcagata agattatgag ggctactgcc aacaattcca aatgtgtgct tctccttgct     480
gtatgctata cttcaactga tgagatcgtg catgctgttg aagaatcctc tgaattgaac     540
tccaatgaag tttgtaacaa tcaagaattg gaggaggcaa atgcaactgg aagcggtact     600
gtgattcaaa ctgagaacat ggagtcgtat tctggaataa acttgtaga ccttgagaaa      660 aacacctaca taaatcctta tcctgatgtt ctgattcgaa cttctgggga gacccgtctg     720
agcaactact tactttggca gactactaat tgcatactgt attctcctta tgcactgtgg     780
ccagagattg gtcttcgaca cgtggtgtgg tcagtaatta acttccaacg tcattattct     840
tacttggaga aacataagga atacttaaaa taa                                  873

<210> SEQ ID NO 8
<211> LENGTH: 290
<212> TYPE: PRT
<213> ORGANISM: Hevea brasiliensis

<400> SEQUENCE: 8

Met Lys Leu Tyr Thr Gly Glu Arg Pro Ser Val Phe Arg Leu Leu Gly
1               5                   10                  15

Lys Tyr Met Arg Lys Gly Leu Tyr Gly Ile Leu Thr Gln Gly Pro Ile
            20                  25                  30

```
Pro Thr His Leu Ala Phe Ile Leu Asp Gly Asn Arg Arg Phe Ala Lys
        35                  40                  45

Lys His Lys Leu Pro Glu Gly Gly His Lys Ala Gly Phe Leu Ala
 50                  55                  60

Leu Leu Asn Val Leu Thr Tyr Cys Tyr Glu Leu Gly Val Lys Tyr Ala
 65                  70                  75                  80

Thr Ile Tyr Ala Phe Ser Ile Asp Asn Phe Arg Arg Lys Pro His Glu
                 85                  90                  95

Val Gln Tyr Val Met Asn Leu Met Leu Glu Lys Ile Glu Gly Met Ile
                100                 105                 110

Met Glu Glu Ser Ile Ile Asn Ala Tyr Asp Ile Cys Val Arg Phe Val
                115                 120                 125

Gly Asn Leu Lys Leu Leu Ser Glu Pro Val Lys Thr Ala Ala Asp Lys
130                 135                 140

Ile Met Arg Ala Thr Ala Asn Asn Ser Lys Cys Val Leu Leu Leu Ala
145                 150                 155                 160

Val Cys Tyr Thr Ser Thr Asp Glu Ile Val His Ala Val Glu Glu Ser
                165                 170                 175

Ser Glu Leu Asn Ser Asn Glu Val Cys Asn Asn Gln Glu Leu Glu Glu
                180                 185                 190

Ala Asn Ala Thr Gly Ser Gly Thr Val Ile Gln Thr Glu Asn Met Glu
                195                 200                 205

Ser Tyr Ser Gly Ile Lys Leu Val Asp Leu Glu Lys Asn Thr Tyr Ile
                210                 215                 220

Asn Pro Tyr Pro Asp Val Leu Ile Arg Thr Ser Gly Glu Thr Arg Leu
225                 230                 235                 240

Ser Asn Tyr Leu Leu Trp Gln Thr Thr Asn Cys Ile Leu Tyr Ser Pro
                245                 250                 255

Tyr Ala Leu Trp Pro Glu Ile Gly Leu Arg His Val Val Trp Ser Val
                260                 265                 270

Ile Asn Phe Gln Arg His Tyr Ser Tyr Leu Glu Lys His Lys Glu Tyr
                275                 280                 285

Leu Lys
    290

<210> SEQ ID NO 9
<211> LENGTH: 1728
<212> TYPE: DNA
<213> ORGANISM: Hevea brasiliensis

<400> SEQUENCE: 9
atggacacca ccggccggct ccaccaccga aagcatgcta caccgttga ggaccgttct    60 ccgaccactc cgaaagcgtc ggacgcgctt ccgcttcccc tctacctgac caacgcggtt   120
ttcttcacgc tgttcttctc ggtggcgtat tacctcctc accggtggcg cgacaagatc   180
cgcaactcca ctccccttca tatcgttact ctctctgaaa ttgttgctat tgtctccctc   240
attgcctctt tcatttacct cctaggattc ttcggtatcg attttgtgca gtcattcatt   300
gcacgcgcct cccatgacgt gtgggacctc gaagatacgg atcccaacta cctcatcgat   360
gaagatcacc gtctcgttac ttgccctccc gctaatatat ctactaagac taccattatt   420
gccgcaccta ccaaattgcc tacctcgaa cccttaattg caccttagt ctcggaggaa   480 gccgcaccta ccaaattgcc tacctcgaa cccttaattg caccttagt ctcggaggaa   480 gacgaaatga tcgtcaactc cgtcgtggat gggaagatac cctcctattc tctggagtcg   540
aagctcgggg actgcaaacg agcggctgcg attcgacgcg aggctttgca gaggatgaca   600
```

```
aggaggtcgc tggaaggctt gccagtagaa gggttcgatt acgagtcgat tttaggacaa      660
tgctgtgaaa tgccagtggg atacgtgcag attccggtgg ggattgcggg gccgttgttg      720
ctgaacgggc gggagtactc tgttccaatg gcgaccacgg agggttgttt ggtggcgagc      780
actaatagag ggtgtaaggc gatttacttg tcaggtgggg ccaccagcgt cttgttgaag      840
gatggcatga caagagcgcc tgttgtaaga ttcgcgtcgg cgactagagc gcggagttg       900 aagttcttct tggaggatcc tgacaatttt gataccttgg ccgtagtttt taacaagtcc      960
agtagatttg cgaggctcca aggcattaaa tgctcaattg ctggtaagaa tctttatata     1020
agattcagct gcagcactgg cgatgcaatg gggatgaaca tggtttctaa aggggttcaa     1080
aacgttcttg aatttcttca aagtgatttt tctgatatgg atgtcattgg aatctcagga     1140
aatttttgtt cggataagaa gcctgctgct gtaaattgga ttgaaggacg tggcaaatca     1200
gttgtttgtg aggcaattat caaggaagag gtggtgaaga aggtgttgaa aaccaatgtg     1260
gcctccctag tggagcttaa catgctcaag aatcttgctg ttctgctgt tgctggtgct      1320 ttgggtggat ttaatgccca tgcaggcaac atcgtatctg caatctttat tgccactggc     1380
caggatccag cacagaatgt tgagagttct cattgcatta ccatgatgga agctgtcaat     1440
gatggaaagg atctccatat ctctgtgacc atgccctcca ttgaggtggg tacagtcgga     1500 ggtgaactc aacttgcatc tcagtctgct tgtctcaatt tgcttggggt gaagggtgca      1560
aacaaagagt cgccaggatc aaactcaagg ctccttgctg ccatcgtagc tggttcagtt     1620
ttggctggtg agctctcctt gatgtctgcc attgcagctg ggcagcttgt caagagtcac     1680
atgaagtaca cagctccag caaagatatg tctaaagctg catcttag                   1728
```

<210> SEQ ID NO 10
<211> LENGTH: 575
<212> TYPE: PRT
<213> ORGANISM: Hevea brasiliensis

<400> SEQUENCE: 10

```
Met Asp Thr Thr Gly Arg Leu His His Arg Lys His Ala Thr Pro Val
1               5                   10                  15

Glu Asp Arg Ser Pro Thr Thr Pro Lys Ala Ser Asp Ala Leu Pro Leu
            20                  25                  30

Pro Leu Tyr Leu Thr Asn Ala Val Phe Phe Thr Leu Phe Phe Ser Val
        35                  40                  45

Ala Tyr Tyr Leu Leu His Arg Trp Arg Asp Lys Ile Arg Asn Ser Thr
    50                  55                  60

Pro Leu His Ile Val Thr Leu Ser Glu Ile Val Ala Ile Val Ser Leu
65                  70                  75                  80

Ile Ala Ser Phe Ile Tyr Leu Leu Gly Phe Gly Ile Asp Phe Val
                85                  90                  95

Gln Ser Phe Ile Ala Arg Ala Ser His Asp Val Trp Asp Leu Glu Asp
            100                 105                 110

Thr Asp Pro Asn Tyr Leu Ile Asp Glu Asp His Arg Leu Val Thr Cys
        115                 120                 125

Pro Pro Ala Asn Ile Ser Thr Lys Thr Thr Ile Ala Ala Pro Thr
        130                 135                 140

Lys Leu Pro Thr Ser Glu Pro Leu Ile Ala Pro Leu Val Ser Glu Glu
145                 150                 155                 160

Asp Glu Met Ile Val Asn Ser Val Val Asp Gly Lys Ile Pro Ser Tyr
                165                 170                 175
```

Ser Leu Glu Ser Lys Leu Gly Asp Cys Lys Arg Ala Ala Ile Arg
            180                 185                 190

Arg Glu Ala Leu Gln Arg Met Thr Arg Arg Ser Leu Glu Gly Leu Pro
        195                 200                 205

Val Glu Gly Phe Asp Tyr Glu Ser Ile Leu Gly Gln Cys Cys Glu Met
210                 215                 220

Pro Val Gly Tyr Val Gln Ile Pro Val Gly Ile Ala Gly Pro Leu Leu
225                 230                 235                 240

Leu Asn Gly Arg Glu Tyr Ser Val Pro Met Ala Thr Thr Glu Gly Cys
                245                 250                 255

Leu Val Ala Ser Thr Asn Arg Gly Cys Lys Ala Ile Tyr Leu Ser Gly
            260                 265                 270

Gly Ala Thr Ser Val Leu Leu Lys Asp Gly Met Thr Arg Ala Pro Val
        275                 280                 285

Val Arg Phe Ala Ser Ala Thr Arg Ala Ala Glu Leu Lys Phe Phe Leu
    290                 295                 300

Glu Asp Pro Asp Asn Phe Asp Thr Leu Ala Val Val Phe Asn Lys Ser
305                 310                 315                 320

Ser Arg Phe Ala Arg Leu Gln Gly Ile Lys Cys Ser Ile Ala Gly Lys
                325                 330                 335

Asn Leu Tyr Ile Arg Phe Ser Tyr Ser Thr Gly Asp Ala Met Gly Met
            340                 345                 350

Asn Met Val Ser Lys Gly Val Gln Asn Val Leu Glu Phe Leu Gln Ser
        355                 360                 365

Asp Phe Ser Asp Met Asp Val Ile Gly Ile Ser Gly Asn Phe Cys Ser
370                 375                 380

Asp Lys Lys Pro Ala Ala Val Asn Trp Ile Glu Gly Arg Gly Lys Ser
385                 390                 395                 400

Val Val Cys Glu Ala Ile Ile Lys Glu Glu Val Val Lys Lys Val Leu
                405                 410                 415

Lys Thr Asn Val Ala Ser Leu Val Glu Leu Asn Met Leu Lys Asn Leu
            420                 425                 430

Ala Gly Ser Ala Val Ala Gly Ala Leu Gly Gly Phe Asn Ala His Ala
        435                 440                 445

Gly Asn Ile Val Ser Ala Ile Phe Ile Ala Thr Gly Gln Asp Pro Ala
    450                 455                 460

Gln Asn Val Glu Ser Ser His Cys Ile Thr Met Met Glu Ala Val Asn
465                 470                 475                 480

Asp Gly Lys Asp Leu His Ile Ser Val Thr Met Pro Ser Ile Glu Val
                485                 490                 495

Gly Thr Val Gly Gly Gly Thr Gln Leu Ala Ser Gln Ser Ala Cys Leu
            500                 505                 510

Asn Leu Leu Gly Val Lys Gly Ala Asn Lys Glu Ser Pro Gly Ser Asn
        515                 520                 525

Ser Arg Leu Leu Ala Ala Ile Val Ala Gly Ser Val Leu Ala Gly Glu
    530                 535                 540

Leu Ser Leu Met Ser Ala Ile Ala Ala Gly Gln Leu Val Lys Ser His
545                 550                 555                 560

Met Lys Tyr Asn Arg Ser Ser Lys Asp Met Ser Lys Ala Ala Ser
                565                 570                 575

<210> SEQ ID NO 11
<211> LENGTH: 705

<212> TYPE: DNA
<213> ORGANISM: Hevea brasiliensis

<400> SEQUENCE: 11

```
atgggtgagg ctccagatgt cggcatggat gctgtccaga acgcctcat gttcgacgat      60
gaatgcattt tagtagatga gaacgatggt gttgttggtc atgcttccaa atataattgt    120
catttgtggg aaaatatttt gaaggggaac gcattacata gagcttttag cgtatttctc    180
ttcaactcaa aatatgagct actccttcag caacgctctg ggacaaaggt gacattcccg    240
cttgtatgga caaacacttg ctgtagtcat cctctgtacc gtgaatctga gcttattgat    300
gaggatgctc ttggtgtgag aaatgctgca caaggaagc ttttcgatga gcttggtatc     360
cctgctgaag atgttccagt tgatcagttt actccactag gacgtatact atataaggcg    420
tcctccgatg gaaagtgggg agagcatgaa cttgattatc tgctctttat agtccgtgat    480
gttaatgtaa atccaaaccc tgatgaggta gctgatgtaa agtatgttaa ccgggatcag    540
ttgaaggagc tcttgaggaa ggcggattct ggcgaggaag gtataaattt gtcaccttgg    600
tttagactag ttgtggacaa cttcttgttg aaatggtggg aaaatgtcga aatgggaca     660
ctcaaggaag cagttgacat gaaaacgatt cacaagttga gttga                    705
```

<210> SEQ ID NO 12
<211> LENGTH: 234
<212> TYPE: PRT
<213> ORGANISM: Hevea brasiliensis

<400> SEQUENCE: 12

```
Met Gly Glu Ala Pro Asp Val Gly Met Asp Ala Val Gln Lys Arg Leu
  1               5                  10                  15

Met Phe Asp Asp Glu Cys Ile Leu Val Asp Glu Asn Asp Gly Val Val
                 20                  25                  30

Gly His Ala Ser Lys Tyr Asn Cys His Leu Trp Glu Asn Ile Leu Lys
             35                  40                  45

Gly Asn Ala Leu His Arg Ala Phe Ser Val Phe Leu Phe Asn Ser Lys
         50                  55                  60

Tyr Glu Leu Leu Leu Gln Gln Arg Ser Gly Thr Lys Val Thr Phe Pro
 65                  70                  75                  80

Leu Val Trp Thr Asn Thr Cys Cys Ser His Pro Leu Tyr Arg Glu Ser
                 85                  90                  95

Glu Leu Ile Asp Glu Asp Ala Leu Gly Val Arg Asn Ala Ala Gln Arg
            100                 105                 110

Lys Leu Phe Asp Glu Leu Gly Ile Pro Ala Glu Asp Val Pro Val Asp
        115                 120                 125

Gln Phe Thr Pro Leu Gly Arg Ile Leu Tyr Lys Ala Ser Ser Asp Gly
    130                 135                 140

Lys Trp Gly Glu His Glu Leu Asp Tyr Leu Leu Phe Ile Val Arg Asp
145                 150                 155                 160

Val Asn Val Asn Pro Asn Pro Asp Glu Val Ala Asp Val Lys Tyr Val
                165                 170                 175

Asn Arg Asp Gln Leu Lys Glu Leu Leu Arg Lys Ala Asp Ser Gly Glu
            180                 185                 190

Glu Gly Ile Asn Leu Ser Pro Trp Phe Arg Leu Val Val Asp Asn Phe
        195                 200                 205

Leu Leu Lys Trp Trp Glu Asn Val Glu Asn Gly Thr Leu Lys Glu Ala
    210                 215                 220
```

Val Asp Met Lys Thr Ile His Lys Leu Ser
225                 230

<210> SEQ ID NO 13
<211> LENGTH: 615
<212> TYPE: DNA
<213> ORGANISM: Hevea brasiliensis

<400> SEQUENCE: 13
atggctgaag aggtggagga agagaggcta aagtatttgg attttgtgcg agcggctgga      60
gtttatgctg tagattcttt ctcaactctc tacctttatg ccaaggacat atctggtcca     120
ttaaaacctg gtgtcgatac tattgagaat gtggtgaaga ccgtggttac tcctgtttat     180
tatattcccc ttgaggctgt caagtttgta gacaaaacgg tggatgtatc ggtcactagc     240
ctagatggcg ttgttccccc agttatcaag caggtgtctg cccaaactta ctcggtagct     300
caagatgctc aagaattgt tcttgatgtg gcttcttcag ttttcaacac tggtgtgcag     360
gaaggcgcaa aagctctgta cgctaatctt gaaccaaaag ctgagcaata tgcggtcatt     420
acctggcgtg ccctcaataa gctgccacta gttcctcaag tggcaaatgt agttgtgcca     480
accgctgttt atttctctga aaagtacaac gatgttgttc gtggcactac tgagcaggga     540
tatagagtgt cctcttattt gcctttgttg cccactgaga aaattactaa ggtgtttgga     600
gatgaggcat cataa                                                     615

<210> SEQ ID NO 14
<211> LENGTH: 204
<212> TYPE: PRT
<213> ORGANISM: Hevea brasiliensis

<400> SEQUENCE: 14

Met Ala Glu Glu Val Glu Glu Arg Leu Lys Tyr Leu Asp Phe Val
1               5                   10                  15

Arg Ala Ala Gly Val Tyr Ala Val Asp Ser Phe Ser Thr Leu Tyr Leu
            20                  25                  30

Tyr Ala Lys Asp Ile Ser Gly Pro Leu Lys Pro Gly Val Asp Thr Ile
        35                  40                  45

Glu Asn Val Val Lys Thr Val Val Thr Pro Val Tyr Tyr Ile Pro Leu
    50                  55                  60

Glu Ala Val Lys Phe Val Asp Lys Thr Val Asp Val Ser Val Thr Ser
65                  70                  75                  80

Leu Asp Gly Val Val Pro Pro Val Ile Lys Gln Val Ser Ala Gln Thr
                85                  90                  95

Tyr Ser Val Ala Gln Asp Ala Pro Arg Ile Val Leu Asp Val Ala Ser
            100                 105                 110

Ser Val Phe Asn Thr Gly Val Gln Glu Gly Ala Lys Ala Leu Tyr Ala
        115                 120                 125

Asn Leu Glu Pro Lys Ala Glu Gln Tyr Ala Val Ile Thr Trp Arg Ala
    130                 135                 140

Leu Asn Lys Leu Pro Leu Val Pro Gln Val Ala Asn Val Val Pro
145                 150                 155                 160

Thr Ala Val Tyr Phe Ser Glu Lys Tyr Asn Asp Val Val Arg Gly Thr
                165                 170                 175

Thr Glu Gln Gly Tyr Arg Val Ser Ser Tyr Leu Pro Leu Leu Pro Thr
            180                 185                 190

Glu Lys Ile Thr Lys Val Phe Gly Asp Glu Ala Ser
        195                 200

```
<210> SEQ ID NO 15
<211> LENGTH: 15
<212> TYPE: DNA
<213> ORGANISM: Artificial Sequenece
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: n is a, c, g, or t

<400> SEQUENCE: 15
ntcgastwts gwgtt                                                        15

<210> SEQ ID NO 16
<211> LENGTH: 16
<212> TYPE: DNA
<213> ORGANISM: Artificial Sequenece
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 16
ngtcgtswga nawgaa                                                       16

<210> SEQ ID NO 17
<211> LENGTH: 15
<212> TYPE: DNA
<213> ORGANISM: Artificial Sequenece
<220> FEATURE:
<223> OTHER INFORMATION: Synthetic primer
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 17
wgtgnagwan canag                                                        15

<210> SEQ ID NO 18
<211> LENGTH: 15
<212> TYPE: DNA
<213> ORGANISM: Artificial Sequenece
<220> FEATURE:
<223> OTHER INFORMATION: Synthetic primer
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
```

<223> OTHER INFORMATION: n is a, c, g, or t

<400> SEQUENCE: 18
sttntastnc tntgc                                                        15

<210> SEQ ID NO 19
<211> LENGTH: 17
<212> TYPE: DNA
<213> ORGANISM: Artificial Sequenece
<220> FEATURE:
<223> OTHER INFORMATION: Synthetic primer
<220> FEATURE:
<221> NAME/KEY: misc_feature
<222> LOCATION: (9)..(9)
<223> OTHER INFORMATION: n is a, c, g, or t

<400> SEQUENCE: 19
sstggstana twatwct                                                      17

<210> SEQ ID NO 20
<211> LENGTH: 16
<212> TYPE: DNA
<213> ORGANISM: Artificial Sequenece
<220> FEATURE:
<223> OTHER INFORMATION: Synthetic primer
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 20
agwgnagwan canaga                                                       16

<210> SEQ ID NO 21
<211> LENGTH: 1565
<212> TYPE: DNA
<213> ORGANISM: Hevea brasiliensis

<400> SEQUENCE: 21
ctctgcttcg cacgagtagc gttctaaatc taccaaggat gattacgaaa ggggaagcaa        60
tccttccagg aatcaaaaaa agggacatgc caatgaatgc tcgttttatt accctacaag      120
tacagtgcaa ggttgggtca gtgaatagag ttattggcac agccatgttt cctgtttcta      180
attcttggga ggttatacac aagtgaattt tgagttacag gctgagggat gaaaagaatg      240
gaattgttac actgtatttg gtagggagaa aagtaagaga ggaaagaaaa tataaagaaa      300
aaataagttt atttttttatt gttttgttta aattgaataa aaaataaaga agcgtaaaaa     360
tattaaaagg aaaataaaaa tattttatct ttttttttctt ttctctttaa aatagagaaa     420
aatgagagga aaatatttaa aagtataaat ataactctat atttaataat ttttttttaaa    480 atttaaaaat aaaattataa ttttattatt cataaaataa ttttttctca aatatttttc      540
tctttcaatc cagataaaaa gaaaaaaaat aattttatt ttcattcttt attttctctc       600

```
ttttaatttt ctttctccct gaaatattcc caaacacagt gttaatgttt ttgtaaaaag    660
gggcaagcag tagcagatca cgtgagaaag aatttgccta tagtattgcc cgtgttcttc    720
ctcgtcatcg ttgttgcggc caacctaatt tatcatggag gagtagtgcc agggatttca    780
cgtttggcgt acttctggtg cttaattaat ttatttgggg ttttgtattt taaaattagg    840
taaaatttct ataattttac aaaaattaac ttatttatt aaaaattaaa agatttagac    900
taaatagcaa aatcacgcaa tgggtttagt gttttaatac gagattagac ataataataa    960
taacacctga tggtcctcta ttttcaatta tttgccaact aaaccacaat caaccatgtt   1020
caacacaatt ggaattctac tgatatatca ttacagctgc caaacatttt atttaggcca   1080
ttaatcaatt ttaattgaac atgctatttt tctatcatca attcagcttc ttttttata   1140 ttaatttaat ttataattaa cactaatgac aaaattagat attaaattta tgagaatgaa   1200
acataaaatt aatatataaa aaatatatta gttttaaaaa taattttaaa tattaaactc   1260
aaaatattat atatatatat atatatatat atatgaaaa ttaaaatttt aaattaaaaa   1320
aatgcagtaa aaaaaaaaaa aataataaag tagctattgg atccaagggt ggtttagaac   1380
gctactcgtg cgaagcaaga gtgaggaaaa tgccaaggac ccgtcacgca cgccacatgt   1440
gtggggagga ggctcccgtt ctcgcattct tataaaaatg tcccagatcc aaatctcctg   1500
aaactaagct catcattccc tcttcctcct ctcccttct ctctcctgcg ccggcatatt   1560
tttac                                                              1565

<210> SEQ ID NO 22
<211> LENGTH: 1352
<212> TYPE: DNA
<213> ORGANISM: Hevea brasiliensis

<400> SEQUENCE: 22
gcagccggtt tggtctgaaa ttgcagatcc gagcgatgat cgaattttca cgaaataaaa     60
tgaaagtaca tacgcgaagt ccacaataac agggttagaa taatatatat atatatatat    120
atatatatta ttttttaaata attattatat atatataata ataattattt aaaaattaag    180
aatgttacac aagtgatgat atattgaaat tttataataa attaaataat cacatgtaaa    240
attaataaca tgtataaatt gagatattac ttttattcat gctatattta ttttttactt    300
taaaaattct ttttttttaa tataaaatta ttaaaatata aattcttaat tttctactta    360
taaaacatat actaatattg gaaactatta caatgtcatc tcattttat tattattatt    420 ttttttata gttcatcttc caattaaaaa gggtaattta caaatcaca atgaaagaaa    480 tgatgatcat gactatataa taaattaatg atatttaagg taataaaaaa aaaacatgaa    540
agtaacataa caaaaagatt ataaagagt cttgatgcac ataaggtaac atttccttcc    600
tcacaaaaat ttttttttt taatataaaa aataatttt ttataaatat aggtgaatca    660
gatgcacata atctctttaa catatatata tatatatata tctaagaaaa aagaaatcaa    720
gaatttatct tttatttccc cattgctaga aaatcagtgc agttactggc tcaacccatt    780
atactgtcag ggtttgcaat tgtggacttt ttatcatcaa tttaggcttt taatcaaccg    840
gataatctgg ttcattttc cttatttta agatacaaa atgggagagt tactataaaa    900
ttcgattaga tttcaaatta aaataaaata ttttcttatt aaaaagatt taaatttaaa    960 tttggttaga atcaaattga accaaagcag ataaatcaaa atagaatcaa agaattctat   1020
ggtctggtat caaaaaccgg ctcagaccaa accggctgcc agcctacttc cacaacccca   1080
```

```
tatatcatag atgtcccttt acataaacgc aaaacaagaa cataaaaatg tctctcacca    1140
ctcgccttct aaatgcccac gtgggtagcg ccaccaccag actctcgtcc tcgcttccct    1200
cctctgcttc tcctcgttat tctcactttc tctctaccca atttgcctct ccttctctca    1260
ttcaattccc tctaactctt aaaccttcgt ctacctcttc gttatctagg gtattttcgt    1320
cttctccatc tgcaatcacc gctacttcca cc                                  1352

<210> SEQ ID NO 23
<211> LENGTH: 533
<212> TYPE: DNA
<213> ORGANISM: Hevea brasiliensis

<400> SEQUENCE: 23
cgtggctaga ttattctagg atttgggtat cgcataattt ttagttacta gtgtttagag      60
ttgcttatat ccaataactt cttaataaca attttaaata aaaatattc ttgtgcgtat     120 caaaaaatt taaaataaaa ccatgacata ttcaatttcc ttaactaggt taaaaatttt     180
tcatgcatta gcatatactt aatttgttga taaatagacc tttgatcaac tctcaacatg     240
accaaagtcc ctccttttt tagtataatt ggtttcaatt gaaagtcgaa ctctagactt     300
tatagtttat gaaatgattt caatactact gggttaatgc tcattggtca aagtactcac     360
agcagtatca agtagtcttt taaggttaaa aaaacttata tatatattaa cgaaagatgc     420
cacttgattt agtgtcacct ccgaaataat caacttaatt tagttattgg atctgagatt     480
ttatttttat atttttttc tgatgagcag gttaagtcag tggtttaagt aaa              533

<210> SEQ ID NO 24
<211> LENGTH: 919
<212> TYPE: DNA
<213> ORGANISM: Hevea brasiliensis

<400> SEQUENCE: 24
aaccgtccac caatctttga gttccagtga gtcatctact ggttgcttga cagatccatc      60
aataaaacca tatttctttt tggcccgtaa tgcagtcagc atagctcgcg cccattcttc     120
gtaattctcg cccttcaact gaacttgggt aatcaagtta tctgggttgt cattcgaatt     180
cagtgtttaa gaactaaaag ttttcttccc tgatccagaa ctctcatttt tcttttcatc     240
aaccatggct ctgataccat gtaaaaaaac taagaaattt tggaataaga attcttatct     300
ttattgcccc agaaataaaa tatatatata aaaaaattac agctaacaaa taggtcccta     360
atcaagctaa actaccaaaa ttgtatcaaa gtcatacaac aaaaggtaaa aacagatatg     420
cacacaaaaa ttcctaaaca aatgccctaa ataaatacaa aataagtgac agctaacagc     480
tgcatttcca ataattaatt taactaataa aatttataat cttaaaaata attttaatat     540
tattgaatta aaatttataa ataaaattaa cactgttaaa attaaagaa aattattaag      600 atttgaatttt ttaagcggtt atttaatttt gaaaacaag gctaacttt tttttatat       660 aatttactaa aaaattcatg aatgaaaaaa aaaatccat aagtaaactt accccatacg      720
ggttatgcac gctaaaccaa taaaacgaaa acacgtttat acactcgttt tcatttccat      780
ctataaatag agagattttgt tttagttttt aaaccataat cagttgatag cttccacagt     840
gttttccgaa aggcaaatct ttttcaaac ttcagcgact gcgttttgaa tttgtgattt      900
ttaaaggaaa ttttcaatt                                                   919
```

METHOD FOR REGULATING EXPRESSION OF SPECIFIC PROTEIN USING CYTOKININ-RESPONSIVE TRANSCRIPTION FACTOR, ISOPRENOID-PRODUCING PLANT HAVING GENE ENCODING CYTOKININ-RESPONSIVE TRANSCRIPTION FACTOR INTRODUCED THEREIN, AND METHOD FOR PRODUCING POLYISOPRENOID USING SAID ISOPRENOID-PRODUCING PLANT

REFERENCE TO SEQUENCE LISTING SUBMITTED VIA EFS-WEB

This application is being filed electronically via EFS-Web and includes an electronically submitted sequence listing in .txt format. The .txt file contains a sequence listing entitled "2015-07-24_5051-0352PUS1_ST25.txt" created on Jul. 24, 2015 and is 50,655 bytes in size. The sequence listing contained in this .txt file is part of the specification and is hereby incorporated by reference herein in its entirety.

TECHNICAL FIELD

The present invention relates to a method of regulating the expression of specific protein(s) by a cytokinin-responsive transcription factor, an isoprenoid-producing plant into which has been introduced a gene encoding a cytokinin-responsive transcription factor, and a method of producing a polyisoprenoid using the isoprenoid-producing plant.

BACKGROUND ART

Nowadays natural rubber (one example of polyisoprenoids) for use in industrial rubber products can be harvested from rubber-producing plants, such as *Hevea brasiliensis* (Para rubber tree) belonging to the family Euphorbiaceae, or *Ficus elastica* (Indian rubber tree) belonging to the family Moraceae.

At present, *Hevea brasiliensis* is practically the only one source of natural rubber for industrial rubber products. *Hevea brasiliensis* is a plant that can grow only in limited areas such as in Southeast Asia and South America. Moreover, *Hevea brasiliensis* requires about seven years from planting to mature enough for rubber extraction, and the period during which natural rubber can be extracted is limited to 20 to 30 years. Although more natural rubber is expected to be needed mainly by developing countries in years to come, for the reason mentioned above it is difficult to greatly increase the production of natural rubber using *Hevea brasiliensis*. Depletion of natural rubber sources is therefore of concern and there are needs for stable natural rubber sources other than mature *Hevea brasiliensis* and for improvement in productivity of natural rubber from *Hevea brasiliensis*.

For example, an approach to improve productivity of natural rubber from *Hevea brasiliensis* is to extract more latex to produce more natural rubber. Specifically, such methods include a method of stimulating the trunk of rubber trees with ethylene or ethephon (2-chloroethylphosphonic acid); and a method of accelerating laticifer differentiation using lanolin containing jasmonic acid, linolenic acid, which is a precursor of jasmonic acid, or the like (see, for example, Non Patent Literature 1).

Unfortunately, if the method of increasing latex production via ethylene stimulation is applied to the trunk for a long term, then cracks may easily be generated in the bark. In addition, the aim of the ethylene stimulation is to allow latex to exude more smoothly from laticifers and is not to directly improve the tree's ability to produce latex, and this method provides only a limited and insufficient increase in latex production.

Although jasmonic acid or the like can be used to accelerate laticifer formation and thereby increase the number of laticifers, this method also has the problem that latex exuding from laticifers can coagulate at the cuts during the collection of latex by tapping, and therefore the produced latex may not be sufficiently collected.

Also known are attempts to promote biosynthesis of isoprenoid compounds in plants, such as by overexpressing a gene involved in the mevalonic acid (MVA) pathway or MEP pathway, which are pathways to isopentenyl diphosphate (IPP) biosynthesis, or a gene downstream in such a pathway (Non Patent Literatures 2 and 3).

These methods, however, only enhance the expression of specific enzymes involved in the above-mentioned pathways, or in other words, partially enhance the polyisoprenoid biosynthesis pathway, rather than enhancing the overall pathway of polyisoprenoid biosynthesis. Thus, there remains room for improvement in terms of enhancing the overall pathway of polyisoprenoid biosynthesis.

It is also known that some factors, including light responses, wound responses, and cold treatment, affect polyisoprenoid biosynthesis. However, it is not specifically known which transcription factor is activated in such a response to regulate polyisoprenoid biosynthesis.

CITATION LIST

Non Patent Literature

Non Patent Literature 1: Hao et al., Annals of Botany, 2000, Vol. 85, pp. 37-43
Non Patent Literature 2: Leon, P. et al., J. Biol. Chem. 276, 22901 (2001)
Non Patent Literature 3: Botella-Pavia, P. et al., Plant. J., 40, 188 (2004)

SUMMARY OF INVENTION

Technical Problem

The present invention was made to overcome the above problems, and an object of the present invention is to provide a method for enhancing the overall pathway of polyisoprenoid biosynthesis. Further objects of the present invention are to provide an isoprenoid-producing plant having an overall enhanced pathway of polyisoprenoid biosynthesis, and to provide a method of producing a polyisoprenoid using the isoprenoid-producing plant.

Solution to Problem

The present invention relates to a method of regulating by a cytokinin-responsive transcription factor the expression of at least one protein selected from the group consisting of hydroxymethylglutaryl-CoA reductase, isopentenyl diphosphate isomerase, cis-prenyltransferase, and small rubber particle protein.

Preferably, the method includes introducing a gene encoding the cytokinin-responsive transcription factor into a host to regulate the expression of the protein in the host.

The gene is preferably either of the following DNAs:
[1] a DNA having the base sequence of SEQ ID NO:1, 3, or 5; and
[2] a DNA encoding a protein with transcription factor activity and capable of hybridizing under stringent conditions to a DNA having a base sequence complementary to the base sequence of SEQ ID NO:1, 3, or 5.

The method is preferably used to enhance the expression of at least one protein selected from the group consisting of hydroxymethylglutaryl-CoA reductase, cis-prenyltransferase, and small rubber particle protein, and more preferably to enhance the expression of hydroxymethylglutaryl-CoA reductase, cis-prenyltransferase, and small rubber particle protein.

The cytokinin-responsive transcription factor is preferably any of the following proteins:

[1] a protein having the amino acid sequence of SEQ ID NO:2, 4, or 6;
[2] a protein having transcription factor activity and having an amino acid sequence containing one or more amino acid substitutions, deletions, insertions and/or additions relative to the amino acid sequence of SEQ ID NO:2, 4, or 6; and
[3] a protein having transcription factor activity and having an amino acid sequence that has at least 80% sequence identity to the amino acid sequence of SEQ ID NO:2, 4, or 6.

The host is preferably an isoprenoid-producing plant.

The present invention also relates to an isoprenoid-producing plant, into which has been introduced a gene encoding a cytokinin-responsive transcription factor.

The gene is preferably either of the following DNAs:
[1] a DNA having the base sequence of SEQ ID NO:1, 3, or 5; and
[2] a DNA encoding a protein with transcription factor activity and capable of hybridizing under stringent conditions to a DNA having a base sequence complementary to the base sequence of SEQ ID NO:1, 3, or 5.

The present invention further relates to a method of producing a polyisoprenoid using the isoprenoid-producing plant.

Advantageous Effects of Invention

The method of the present invention, which involves regulating by a cytokinin-responsive transcription factor the expression of at least one protein selected from the group consisting of hydroxymethylglutaryl-CoA reductase, isopentenyl diphosphate isomerase, cis-prenyltransferase, and small rubber particle protein, can enhance the overall pathway of polyisoprenoid biosynthesis. Moreover, the isoprenoid-producing plant of the present invention, into which has been introduced a gene encoding a cytokinin-responsive transcription factor, has an overall enhanced pathway of polyisoprenoid biosynthesis, and the use of the isoprenoid-producing plant for the production of polyisoprenoids allows for increased polyisoprenoid production.

BRIEF DESCRIPTION OF DRAWINGS

FIG. 1 is a schematic view of a part of the polyisoprenoid biosynthesis pathway.

DESCRIPTION OF EMBODIMENTS

The present inventors have made various studies to enhance the overall pathway of polyisoprenoid biosynthesis. FIG. 1 shows a part of the polyisoprenoid biosynthesis pathway. There are two known pathways for biosynthesis of isopentenyl diphosphate (IPP), which is an important member of the polyisoprenoid biosynthesis pathway: mevalonic acid (MVA) pathway (cytosol MVA pathway shown in FIG. 1); and MEP pathway (plastidial DXP pathway shown in FIG. 1).

The present inventors focused on the MVA pathway, which is considered to be a common pathway that supplies IPP in rubber latex synthesis, and selected, from various proteins involved in the polyisoprenoid biosynthesis pathway, some proteins that are expected to play important roles in view of enhancing the entire pathway enclosed by the dotted line in FIG. 1 or the entire downstream pathway.

Specifically, the following four proteins were selected: hydroxymethylglutaryl-CoA reductase (HMG-CoA reductase) that is a rate-limiting factor in the MVA pathway, which is a pathway to IPP biosynthesis; isopentenyl diphosphate isomerase (IPP isomerase) that is involved in isomerization of IPP; cis-prenyltransferase that is thought to be involved in isoprenoid chain elongation; and small rubber particle protein (SRPP) that is known to be involved in polyisoprenoid biosynthesis.

In order to simultaneously regulate the expression of the four proteins, that is, to comprehensively regulate the expression of the four proteins, the present inventors sought a transcription factor capable of regulating (or comprehensively regulating) the expression of all the four proteins. Specifically, DNA fragments from leaves of *Hevea brasiliensis* which contain genes encoding the four proteins (the amino acid sequences of cis-prenyltransferase, HMG-CoA reductase, IPP isomerase, and SRPP are set forth in the sequence listing as SEQ ID NOs:8, 10, 12, and 14, respectively) (the base sequences of the genes encoding cis-prenyltransferase, HMG-CoA reductase, IPP isomerase, and SRPP are set forth in the sequence listing as SEQ ID NOs:7, 9, 11, and 13, respectively) and their promoter regions were cloned (see EXAMPLES for details). The base sequences of the resulting DNA fragments were analyzed to reveal the base sequences of the promoter regions of the genes encoding the proteins.

Additionally, the revealed base sequences of the promoter regions of the four proteins were analyzed using a plant promoter database (a database of plant cis-acting regulatory DNA elements (PLACE)). The analysis revealed that the sequences contain many transcription factor binding sites involved in responses to cytokinins, which are a class of plant growth hormones, (cytokinin responses) and, in particular, the promoter regions of three genes (IPP isomerase, SRPP, cis-prenyltransferase), among the four genes analyzed, all contain a lot of ARR1AT sequences (NGATT) to which ARR1 (the base sequence and the amino acid sequence of ARR1 from *Arabidopsis thaliana* are set forth in the sequence listing as SEQ ID NOs:1 and 2, respectively) binds. The number of ARR1AT sequences is the second largest for IPP isomerase and SRPP, and the fourth largest for cis-prenyltransferase among the transcription factor binding sequences found in each case.

These results strongly suggest that the cytokinin-responsive transcription factor ARR1 is a transcription factor capable of regulating the expression of all the four proteins, or in other words, a transcription factor capable of regulating the overall pathway of polyisoprenoid biosynthesis. Then a validation test using yeast cells was performed to confirm that the expression of the four proteins can be enhanced not only by the use of ARR1 but also by the use of ARR2 (the base sequence and the amino acid sequence of ARR2 from *Arabidopsis thaliana* are set forth in the sequence listing as SEQ ID NOs:3 and 4, respectively) or ARR12 (the base sequence and the amino acid sequence of ARR12 from *Arabidopsis thaliana* are set forth in the sequence listing as SEQ ID NOs:5 and 6, respectively), which, similarly to ARR1, are cytokinin-responsive transcription factors (specifically, type-B ARR-responsive transcription factors).

As described above, the present inventors have found that cytokinin-responsive transcription factors such as ARR1 (in particular, type-BARR-responsive transcription factors) are capable of comprehensively enhancing the expression of HMG-CoA reductase, IPP isomerase, cis-prenyltransferase, and SRPP, and thus capable of enhancing the overall pathway of polyisoprenoid biosynthesis. Another finding is that since the cytokinin-responsive transcription factors such as ARR1 (in particular, type-B ARR-responsive transcription factors) can enhance the overall pathway of polyisoprenoid biosynthesis, an isoprenoid-producing plant into which has been introduced a gene encoding any of the cytokinin-responsive transcription factors (in particular, type-B ARR-responsive transcription factors) can be used for the production of polyisoprenoids to increase polyisoprenoid production.

Theoretically, it is desirable to enhance the expression of HMG-CoA reductase, cis-prenyltransferase and SRPP while suppressing the expression of IPP isomerase. However, although the cytokinin-responsive transcription factors such as ARR1 (in particular, type-BARR-responsive transcription factors) enhance the expression of IPP isomerase as well as the expression of HMG-CoA reductase, cis-prenyltransferase and SRPP, polyisoprenoid production can be successfully increased because the overall pathway of polyisoprenoid biosynthesis is enhanced.

The term "hydroxymethylglutaryl-CoA reductase (HMG-CoA reductase)" as used herein refers to a rate-limiting enzyme of the mevalonic acid pathway and includes both hydroxymethylglutaryl-CoA reductase (NADPH) (EC 1.1.1.34) and hydroxymethylglutaryl-CoA reductase (EC 1.1.1.88).

The term "isopentenyl diphosphate isomerase (IPP isomerase)" as used herein refers to an enzyme that catalyzes the isomerization between isopentenyl diphosphate (IPP) and its isomer, dimethylallyl pyrophosphate (DMAPP).

The term "cis-prenyltransferase" as used herein refers to an enzyme that catalyzes cis-chain elongation of isoprenoid compounds.

The term "small rubber particle protein (SRPP)" as used herein refers to a small rubber particle-associated protein which is associated with small rubber particles of 10 μm or less in diameter in the latex of *Hevea brasiliensis* or the like.

The method of the present invention involves regulating by a cytokinin-responsive transcription factor the expression of at least one protein selected from the group consisting of hydroxymethylglutaryl-CoA reductase, isopentenyl diphosphate isomerase, cis-prenyltransferase, and small rubber particle protein.

The cytokinin-responsive transcription factor is not particularly limited, provided that it is a transcription factor that can be activated in response to cytokinins, which are a class of phytohormones. Examples include transcription factors of the type-B ARR family such as ARR1 (the base sequence and the amino acid sequence of ARR1 from *Arabidopsis thaliana* are set forth in the sequence listing as SEQ ID NOs:1 and 2, respectively), ARR2 (the base sequence and the amino acid sequence of ARR2 from *Arabidopsis thaliana* are set forth in the sequence listing as SEQ ID NOs:3 and 4, respectively), ARR12 (the base sequence and the amino acid sequence of ARR12 from *Arabidopsis thaliana* are set forth in the sequence listing as SEQ ID NOs:5 and 6, respectively), ARR10, ARR14, and ARR18.

The term "transcription factor" as used herein refers to a protein having an activity of increasing or decreasing the rate of transcription of a gene or genes.

The origin of the cytokinin-responsive transcription factor is not particularly limited, but preferred are transcription factors from *Hevea brasiliensis, Sonchus oleraceus, Parthenium argentatum, Taraxacum koksaghyz,* or *Arabidopsis thaliana.*

(Amino Acid Sequence of Cytokinin-Responsive Transcription Factor)

The following protein [1] is a specific example of the cytokinin-responsive transcription factor:
[1] a protein having the amino acid sequence of SEQ ID NO:2, 4, or 6.

Moreover, it is known that some transcription factors have transcription factor activity even when one or more amino acid substitutions, deletions, insertions, or additions are introduced into their original amino acid sequences. Considering this fact, another specific example of the cytokinin-responsive transcription factor is the following protein [2]:
[2] a protein having transcription factor activity and having an amino acid sequence containing one or more amino acid substitutions, deletions, insertions and/or additions relative to the amino acid sequence of SEQ ID NO:2, 4, or 6.

The term "transcription factor activity" as used herein refers to an activity of increasing or decreasing the rate of transcription of at least one gene selected from the group consisting of genes encoding hydroxymethylglutaryl-CoA reductase, isopentenyl diphosphate isomerase, cis-prenyltransferase, and small rubber particle protein.

For maintaining transcription factor activity, the number of amino acid substitutions, deletions, insertions, and/or additions relative to the amino acid sequence of SEQ ID NO:2 is preferably 1 or more, more preferably 1 to 138, still more preferably 1 to 104, particularly preferably 1 to 69, most preferably 1 to 35, even most preferably 1 to 14, and still even most preferably 1 to 7.

Also for maintaining transcription factor activity, the number of amino acid substitutions, deletions, insertions, and/or additions relative to the amino acid sequence of SEQ ID NO:4 is preferably 1 or more, more preferably 1 to 133, still more preferably 1 to 100, particularly preferably 1 to 66, most preferably 1 to 33, even most preferably 1 to 13, and still even most preferably 1 to 7.

Also for maintaining transcription factor activity, the number of amino acid substitutions, deletions, insertions, and/or additions relative to the amino acid sequence of SEQ ID NO:6 is preferably 1 or more, more preferably 1 to 119, still more preferably 1 to 89, particularly preferably 1 to 60, most preferably 1 to 30, even most preferably 1 to 12, and still even most preferably 1 to 6.

Among other amino acid substitutions, conservative substitutions are preferred. Specific examples include substitutions within each of the following groups in the parentheses: (glycine, alanine), (valine, isoleucine, leucine), (aspartic acid, glutamic acid), (asparagine, glutamine), (serine, threonine), (lysine, arginine) and (phenylalanine, tyrosine).

The amino acid substitutions, deletions, insertions, and/or additions are preferably introduced into regions other than cytokinin-responsive transcription factor activity domains, binding domains that bind to transcription factor binding sites, and other important portions involved in transcription factor activity. Those skilled in the art can appropriately identify such domains by homology analysis with a known cytokinin-responsive transcription factor.

It is also known that some proteins with amino acid sequences having high sequence identity to the amino acid sequence of a transcription factor also have similar activity. Considering this fact, another specific example of the cytokinin-responsive transcription factor is the following protein [3]:

[3] a protein having transcription factor activity and having an amino acid sequence that has at least 80% sequence identity to the amino acid sequence of SEQ ID NO:2, 4, or 6.

For maintaining transcription factor activity, the sequence identity to the amino acid sequence of SEQ ID NO: 2, 4, or 6 is preferably at least 85%, more preferably at least 90%, still more preferably at least 95%, particularly preferably at least 98%, and most preferably at least 99%.

The sequence identity between amino acid sequences or base sequences may be determined using the algorithm BLAST® [Pro. Natl. Acad. Sci. USA, 90, 5873 (1993)] developed by Karlin and Altschul or FASTA [Methods Enzymol., 183, 63 (1990)].

Whether a protein has transcription factor activity may be determined by conventionally known techniques, such as gel shift assays, or reporter assays using a reporter gene encoding β-galactosidase, luciferase, or GFP (green fluorescent protein).

The cytokinin-responsive transcription factor is preferably any of the following proteins:

[1-1] a protein having the amino acid sequence of SEQ ID NO:2 or 4;

[2-1] a protein having transcription factor activity and having an amino acid sequence containing one or more amino acid substitutions, deletions, insertions, and/or additions relative to the amino acid sequence of SEQ ID NO:2 or 4; and

[3-1] a protein having transcription factor activity and having an amino acid sequence that has at least 80% sequence identity to the amino acid sequence of SEQ ID NO:2 or 4.

The cytokinin-responsive transcription factor is more preferably any of the following proteins:

[1-2] a protein having the amino acid sequence of SEQ ID NO:2;

[2-2] a protein having transcription factor activity and having an amino acid sequence containing one or more amino acid substitutions, deletions, insertions, and/or additions relative to the amino acid sequence of SEQ ID NO:2; and

[3-2] a protein having transcription factor activity and having an amino acid sequence that has at least 80% sequence identity to the amino acid sequence of SEQ ID NO:2.

(DNA Encoding Cytokinin-Responsive Transcription Factor)

Moreover, the DNA encoding the cytokinin-responsive transcription factor may be either of the following DNAs:

[1] a DNA having the base sequence of SEQ ID NO:1, 3, or 5; and

[2] a DNA encoding a protein with transcription factor activity and capable of hybridizing under stringent conditions to a DNA having a base sequence complementary to the base sequence of SEQ ID NO:1, 3, or 5.

As used herein, the term "hybridizing" means a process in which the DNA hybridizes to a DNA having a particular base sequence or a part of the DNA. Thus, the DNA having a particular base sequence or part of the DNA may have a base sequence long enough to be usable as a probe in Northern or Southern blot analysis or as an oligonucleotide primer in polymerase chain reaction (PCR) analysis. The DNA used as a probe may have a length of at least 100 bases, preferably at least 200 bases, and more preferably at least 500 bases although it may be a DNA of at least 10 bases, and preferably of at least 15 bases in length.

Techniques to perform DNA hybridization experiments are well known. The hybridization conditions under which experiments are performed may be determined according to, for example, Molecular Cloning, 2nd ed. and 3rd ed. (2001), Methods for General and Molecular Bacteriology, ASM Press (1994), Immunology methods manual, Academic press (Molecular), and many other standard textbooks.

The stringent conditions may include, for example, an overnight incubation at 42° C. of a DNA-immobilized filter and a DNA probe in a solution containing 50% formamide, 5×SSC (750 mM sodium chloride and 75 mM sodium citrate), 50 mM sodium phosphate (pH 7.6), 5×Denhardt's solution, 10% dextran sulfate, and 20 µg/l denatured salmon sperm DNA, followed by washing the filter for example in a 0.2×SSC solution at approximately 65° C. Less stringent conditions may also be used. Changes in the stringency may be accomplished through the manipulation of formamide concentration (lower percentages of formamide result in lower stringency), salt concentrations or temperature. For example, low stringent conditions include an overnight incubation at 37° C. in a solution containing 6×SSCE (20×SSCE: 3 mol/l sodium chloride, 0.2 mol/l sodium dihydrogen phosphate, 0.02 mol/l EDTA, pH 7.4), 0.5% SDS, 30% formamide, and 100 µg/l denatured salmon sperm DNA, followed by washing in a 1×SSC solution containing 0.1% SDS at 50° C. In addition, to achieve even lower stringency, washes performed following hybridization may be done at higher salt concentrations (e.g. 5×SSC) in the above-mentioned low stringent conditions.

Variations in the above various conditions may be accomplished through the inclusion or substitution of blocking reagents used to suppress background in hybridization experiments. The inclusion of blocking reagents may require modification of the hybridization conditions for compatibility.

The DNA capable of hybridization under stringent conditions described above may be a DNA having a base sequence that has at least 80%, preferably at least 90%, more preferably at least 95%, even more preferably at least 98%, and particularly preferably at least 99% sequence identity to the base sequence of SEQ ID NO: 1, 3, or 5 as calculated using a program such as BLAST® or FASTA with parameters mentioned above.

Whether the DNA capable of hybridizing under stringent conditions to the DNA mentioned above encodes a protein with transcription factor activity may be determined by conventionally known techniques, such as gel shift assays or reporter assays using a reporter gene encoding β-galactosidase, luciferase, or GFP (green fluorescent protein).

The DNA encoding the cytokinin-responsive transcription factor is preferably either of the following DNAs:

[1-1] a DNA having the base sequence of SEQ ID NO:1 or 3; and

[2-1] a DNA encoding a protein with transcription factor activity and capable of hybridizing under stringent conditions to a DNA having a base sequence complementary to the base sequence of SEQ ID NO:1 or 3.

More preferred is either of the following DNAs:

[1-2] a DNA having the base sequence of SEQ ID NO:1; and

[2-2] a DNA encoding a protein with transcription factor activity and capable of hybridizing under stringent conditions to a DNA having a base sequence complementary to the base sequence of SEQ ID NO:1.

The cytokinin-responsive transcription factor and the DNA encoding the cytokinin-responsive transcription factor may be obtained by site-directed mutagenesis of, for example, the base sequence of SEQ ID NO:1, 3, or 5 (the base sequence of ARR1 from *Arabidopsis thaliana*, the base sequence of ARR2 from *Arabidopsis thaliana*, or the base sequence of ARR12 from *Arabidopsis thaliana*) according to site-directed mutagenesis techniques described in Molecular Cloning, A Laboratory Manual, Second Edition, Cold Spring Harbor Laboratory Press (1989), Current Protocols in Molecular Biology, John Wiley & Sons (1987-1997), Nucleic Acids Research, 10, 6487 (1982), Proc. Natl. Acad. Sci. USA, 79, 6409 (1982), Gene, 34, 315 (1985), Nucleic Acids Research, 13, 4431 (1985), Proc. Natl. Acad. Sci. USA, 82, 488 (1985), etc.

(Transformant)

The gene encoding the cytokinin-responsive transcription factor can be introduced into a host to create an organism (transformant) that is transformed to express the cytokinin-responsive transcription factor. Then this transformant expresses the cytokinin-responsive transcription factor and is thereby capable of the regulated (enhanced) expression of at least one protein selected from the group consisting of hydroxymethylglutaryl-CoA reductase, isopentenyl diphosphate isomerase, cis-prenyltransferase, and small rubber particle protein (preferably at least one protein selected from the group consisting of hydroxymethylglutaryl-CoA reductase, cis-prenyltransferase, and small rubber particle protein).

More specifically, the transformant is capable of the comprehensively enhanced expression of the four proteins: hydroxymethylglutaryl-CoA reductase, isopentenyl diphosphate isomerase, cis-prenyltransferase, and small rubber particle protein (preferably the three proteins: hydroxymethylglutaryl-CoA reductase, cis-prenyltransferase, and small rubber particle protein). Therefore, the transformant has an overall enhanced pathway of polyisoprenoid biosynthesis and allows for increased polyisoprenoid production.

The following briefly describes how to prepare an organism (transformant) that is transformed to express a cytokinin-responsive transcription factor. The brief description below mainly focuses on how to prepare a transformant that is transformed to express the above-mentioned cytokinin-responsive transcription factor. Once a cytokinin-responsive transcription factor-encoding gene to be introduced has been determined, such a transformant can be prepared by known methods.

Specifically, for example, a DNA containing the base sequence of SEQ ID NO:1, 3, or 5 (the base sequence of ARR1 from *Arabidopsis thaliana*, the base sequence of ARR2 from *Arabidopsis thaliana*, or the base sequence of ARR12 from *Arabidopsis thaliana*) is inserted downstream of a promoter of an appropriate expression vector using appropriate restriction enzymes and the like to prepare a recombinant DNA, which is then introduced into host cells compatible with the expression vector to obtain a transformant.

Although the above description relates to the cases where a DNA containing the base sequence of SEQ ID NO: 1, 3, or 5 (the base sequence of ARR1 from *Arabidopsis thaliana*, the base sequence of ARR2 from *Arabidopsis thaliana*, or the base sequence of ARR12 from *Arabidopsis thaliana*) is used, a DNA encoding any of other cytokinin-responsive transcription factors from *Arabidopsis thaliana* or cytokinin-responsive transcription factors from organisms other than *Arabidopsis thaliana* may be used. In such cases, screening may be performed by a known method using, for example, a part of the base sequence of SEQ ID NO: 1 as a probe to identify and isolate a DNA encoding a particular cytokinin-responsive transcription factor. The method for isolating a DNA molecule of interest using a DNA molecule as a probe is described in, for example, Molecular Cloning, 2nd edition, Cold Spring Harbor Press (1989). DNAs obtained by mutagenesis of the DNAs mentioned above may also be used.

Any of microorganisms, yeasts, animal cells, insect cells, plant cells, and the like can be used as the host (host cells), as long as they are capable of expressing a gene of interest. Since the only organisms currently known to biosynthesize polyisoprenoids are plants (isoprenoid-producing plants), the host is preferably a plant (an isoprenoid-producing plant), and the host cells are preferably plant cells (cells of an isoprenoid-producing plant). Please note that if a future advance in technology allows cells other than plant cells to biosynthesize polyisoprenoids, the gene encoding the cytokinin-responsive transcription factor can be suitably introduced into such cells.

The isoprenoid-producing plant is not particularly limited, provided that it is capable of producing an isoprenoid. Examples include plants of the genus *Hevea*, such as *Hevea brasiliensis*; plants of the genus *Sonchus*, such as *Sonchus oleraceus*, *Sonchus asper*, and *Sonchus brachyotus*; plants of the genus *Solidago*, such as *Solidago altissima*, *Solidago virgaurea* subsp. *asiatica*, *Solidago virgaurea* subsp. *leipcarpa*, *Solidago virgaurea* subsp. *leipc arpaf. paludosa*, *Solidago virgaurea* subsp. *gigantea*, and *Solidago gigantea* Ait. var. *leiophylla* Fernald; plants of the genus *Helianthus*, such as *Helianthus annuus*, *Helianthus argophyllus*, *Helianthus atrorubens*, *Helianthus debilis*, *Helianthus decapetalus*, and *Helianthus giganteus*; plants of the genus *Taraxacum*, such as *Taraxacum*, *Taraxacum venustum* H. Koidz, *Taraxacum hondoense* Nakai, *Taraxacum platycarpum* Dahlst, *Taraxacum japonicum*, *Taraxacum officinale* Weber, and *Taraxacum koksaghyz*; plants of the genus *Ficus*, such as *Ficus carica*, *Ficus elastica*, *Ficus pumila* L., *Ficus erecta* Thumb., *Ficus ampelas* Burm. f., *Ficus benguetensis* Merr., *Ficus irisana* Elm., *Ficus microcarpa* L.f., *Ficus septica* Burm. f., and *Ficus benghalensis*; plants of the genus *Parthenium*, such as *Parthenium argentatum*, *Parthenium hysterophorus*, and *Parthenium hysterophores*; and *Lactuca serriola* and *Ficus benghalensis*. In particular, the isoprenoid-producing plant is preferably at least one selected from the group consisting of plants of the genera *Hevea*, *Sonchus*, *Taraxacum* and *Parhenium*, and more preferably at least one selected from the group consisting of *Hevea brasiliensis*, *Sonchus oleraceus*, *Parthenium argentatum*, and *Taraxacum koksaghyz*.

Examples of expression vectors that can be used include vectors that are capable of autonomous replication in the host cells or of being incorporated into a chromosome thereof and contain a promoter at a position that permits transcription of the recombinant DNA.

In cases where plant cells are used as host cells, a pBI vector, a pUC vector, a Ti plasmid or tobacco mosaic virus vector, for example, may be used as an expression vector.

Any promoter that functions in plant cells can be used. Examples include cauliflower mosaic virus (CaMV) 35S promoter and rice actin-1 promoter, nopaline synthase gene promoter, tobacco mosaic virus 35S promoter, and rice actin gene promoter.

Preferred are expression vectors with promoters that are specifically expressed in tissues in which isoprenoid compounds are biosynthesized, such as laticifers. When the promoter is specifically expressed in tissues in which polyisoprenoids are biosynthesized, retardation of plant growth and other adverse effects can be prevented.

The recombinant vector can be introduced by any method that allows the DNA to be introduced into plant cells. Examples include methods using *Agrobacterium* (JP S59-140885 A, JP S60-70080 A, WO94/00977), electroporation (JP S60-251887 A), and methods using a particle gun (gene gun) (JP 2606856 B, JP 2517813 B).

A transformant (transgenic plant cells) into which has been introduced the gene encoding the cytokinin-responsive transcription factor can be prepared by these methods or the like.

The present invention provides an isoprenoid-producing plant into which has been introduced a gene encoding a cytokinin-responsive transcription factor. The isoprenoid-producing plant is not particularly limited, as long as it is an isoprenoid-producing plant containing transgenic plant cells. The transgenic plant cells are intended to include, in addition to transgenic plant cells prepared by the above-described methods, for example, all their progeny or clones and even progeny plants obtained by passaging these cells. Once transgenic plant cells into which the DNA or vector has been introduced in the genome are obtained, progeny or clones can be obtained from the transgenic plant cells by sexual or asexual reproduction, tissue culture, cell culture, cell fusion, or the like. Further, the transgenic plant cells, or progeny or clones thereof may be used to obtain reproductive materials (e.g. seeds, fruits, cuttings, stem tubers, root tubers, shoots, adventitious buds, adventitious embryos, calluses, protoplasts) which can then be used to produce the isoprenoid-producing plant on a large scale.

Techniques to regenerate plants from transgenic plant cells are already known; for example, Doi et al. disclose techniques for *eucalyptus* (Japanese Patent Application No. H11-127025), Fujimura et al. disclose techniques for rice (Fujimura et al., (1995), Plant Tissue Culture Lett., vol. 2: p 74-), Shillito et al. disclose techniques for corn (Shillito et al., (1989), Bio/Technology, vol. 7: p 581-), Visser et al. discloses techniques for potato (Visser et al., (1989), Theor. Appl. Genet., vol. 78: p 589-), and Akama et al. disclose techniques for *Arabidopsis thaliana* (Akama et al., (1992), Plant Cell Rep., vol. 12: p 7-). Those skilled in the art can regenerate plants from transgenic plant cells according to these documents.

Whether a target transcription factor gene is expressed in a regenerated plant may be determined by well-known methods. For example, western blot analysis may be used to assess the expression of a target transcription factor.

Seeds can be obtained from the transgenic plant, for example, as follows: the transgenic plant is rooted in an appropriate medium and then transplanted to water-containing soil in a pot, and grown under proper cultivation conditions so as to finally produce seeds, which are then collected. Further, plants can be grown from seeds, for example, as follows: seeds obtained from the transgenic plant as described above are sown in water-containing soil, and grown under proper cultivation conditions into plants.

According to the present invention, the isoprenoid-producing plant into which has been introduced a gene encoding a cytokinin-responsive transcription factor can be used for the production of polyisoprenoids to increase polyisoprenoid production. Specifically, polyisoprenoids can be produced by culturing transgenic plant cells prepared as described above, calluses obtained from such transgenic plant cells, cells redifferentiated from such calluses, or the like in an appropriate medium, or by growing transgenic plants regenerated from the transgenic plant cells, plants grown from seeds collected from such transgenic plants, or the like under proper cultivation conditions. The isoprenoid-producing plant of the present invention has a polyisoprenoid biosynthesis pathway enhanced overall by the cytokinin-responsive transcription factor introduced therein, and thereby allows for increased polyisoprenoid production.

The term "polyisoprenoid" as used herein is a generic term used to refer to polymers having isoprene ($C_5H_8$) units. Examples of polyisoprenoids include polymers such as monoterpenes ($C_{10}$), sesquiterpenes ($C_{15}$), diterpenes ($C_{20}$), sesterterpenes ($C_{25}$), triterpenes ($C_{30}$), tetraterpenes ($C_{40}$), and natural rubber.

The present invention enables to regulate (enhance) by a cytokinin-responsive transcription factor the expression of at least one protein selected from the group consisting of hydroxymethylglutaryl-CoA reductase, isopentenyl diphosphate isomerase, cis-prenyltransferase, and small rubber particle protein, as described above, and thus makes it possible to enhance the overall pathway of polyisoprenoid biosynthesis to increase polyisoprenoid production.

Moreover, the isoprenoid-producing plant of the present invention into which has been introduced a gene encoding a cytokinin-responsive transcription factor has an overall enhanced pathway of polyisoprenoid biosynthesis, and the use of the isoprenoid-producing plant for the production of polyisoprenoids allows for increased polyisoprenoid production.

As described above, the method of the present invention, the isoprenoid-producing plant of the present invention, and the method of producing a polyisoprenoid of the present invention, which are capable of increasing polyisoprenoid production, can be effective for natural rubber source depletion that is of concern.

EXAMPLES

The present invention will be specifically described by reference to examples. The examples are not to be construed as limiting the present invention.

(Preparation of Promoter Sequence)

DNA fragments containing the gene encoding HMG-CoA reductase, IPP isomerase, cis-prenyltransferase, or small rubber particle protein from leaves of *Hevea brasiliensis* (the base sequences of the genes encoding cis-prenyltransferase, HMG-CoA reductase, IPP isomerase, and SRPP are set forth in the sequence listing as SEQ ID NOs:7, 9, 11, and 13, respectively) and its promoter were cloned in the following manner. First, genomic DNA was extracted from leaves of *Hevea brasiliensis*. The extraction was carried out using a commercial genomic DNA extraction kit. The genes with their promoter regions were amplified by TAIL-PCR using random primers shown as Primers 1 to 6 and primers corresponding to the genes.

```
Primer 1:
                              (SEQ ID NO: 15)
5'-ntcgastwtsgwgtt-3'

Primer 2:
                              (SEQ ID NO: 16)
5'-ngtcgtswganawgaa-3'

Primer 3:
                              (SEQ ID NO: 17)
5'-wgtgnagwancanag-3'
```

-continued

Primer 4:
(SEQ ID NO: 18)
5'-sttntastnctntgc-3'

Primer 5:
(SEQ ID NO: 19)
5'-sstggstanatwatwct-3'

Primer 6:
(SEQ ID NO: 20)
5'-agwgnagwancanaga-3'

The base sequences of the DNA fragments obtained using the primers were analyzed to determine the presence of the promoter sequences of HMG-CoA reductase, IPP isomerase, cis-prenyltransferase, and small rubber particle protein. The base sequence of the promoter sequence of HMG-CoA reductase, the base sequence of the promoter sequence of IPP isomerase, the base sequence of the promoter sequence of cis-prenyltransferase, and the base sequence of the promoter sequence of small rubber particle protein are shown as SEQ ID NOs:21 to 24, respectively.

The promoter sequences were analyzed using a plant promoter database (a database of plant cis-acting regulatory DNA elements (PLACE)) (www.dna.affrc.go.jp/PLACE/).

The analysis revealed that the sequences contain many transcription factor binding sites involved in cytokinin responses, and, in particular, the promoter sequences of three genes (IPP isomerase, small rubber particle protein, and cis-prenyltransferase), among the four genes analyzed, all contain a lot of ARR1AT sequences (NGATT) to which ARR1 binds. The number of ARR1AT sequences is the second largest for IPP isomerase and small rubber particle protein, and the fourth largest for cis-prenyltransferase among the transcription factor binding sequences found in each case.

(Amplification of Promoter Region)

As the promoter regions of the genes, the following regions were amplified by PCR.
HMG-CoA reductase promoter: −1 to −1500 bp, −1 to −1000 bp, and −1 to −500 bp
IPP isomerase promoter: −1 to −1000 bp, and −1 to −500 bp
Cis-prenyltransferase promoter: −1 to −500 bp
Small rubber particle protein promoter: −1 to −1000 bp, and −1 to −500 bp The PCR products were each cloned into pMD20T (Takara Bio, Inc.) to construct pMD20T-hmgpro (−1500), pMD20T-hmgpro (−1000), pMD20T-hmgpro (−500), pMD20T-ipppro (−1000), pMD20T-ipppro (−500), pMD20T-cptpro (−500), pMD20T-srpppro (−1000), and pMD20T-srpppro (−500). The inserted PCR products were sequenced to confirm that no mutation was introduced.

(Construction of Reporter Sequence-Containing Vector)

The plasmids constructed in (Amplification of promoter region) were restricted with SpeI and any of HindIII, KpnI and BamHI, and the promoter sequence fragments were individually incorporated at a site of pYES3/CT/LacZ from which the T7 promoter region had been removed, that is, immediately upstream of the lacZ reporter gene to construct pYES3-hmgprolacZ (−1500), pYES3-hmgprolacZ (−1000), pYES3-hmgpro (−500), pYES3-ippprolacZ (−1000), pYES3-ippprolacZ (−500), pYES3-cptprolacZ (−500), pYES3-srppprolacZ (−1000), and pYES3-srppprolacZ (−500). Ligation high ver. 2 (TOYOBO) was used for ligation.

(Construction of Vector for Gene Introduction into Yeast Chromosome)

The sequence from the SpeI site to the CYC1 transcription termination signal of each of the plasmids constructed in (Construction of reporter sequence-containing vector) was amplified by PCR, and each fragment was restricted with SalI, SmaI, XbaI or SphI, thereby providing DNA fragments with the promoter sequences each linked to the lacZ gene. In order to allow the obtained DNA fragments to be inserted into a yeast chromosome, the DNA fragments were individually incorporated into pAUR101 DNA (Takara Bio, Inc.) restricted in the same manner to construct pAUR101-hmgprolacZ (−1500), pAUR101-hmgprolacZ (−1000), pAUR101-hmgpro (−500), pAUR101-ippprolacZ (−1000), pAUR101-ippprolacZ (−500), pAUR101-cptprolacZ (−500), pAUR101-srppprolacZ (−1000), and pAUR101-srppprolacZ (−500). Ligation high ver.2 was used for ligation as above.

(Acquisition of Transcription Factor Gene)

Next, PCR was performed using an *Arabidopsis thaliana* cDNA library as a template. The PCR produced the following three PCR fragments: At3g16857 (ARR1) (SEQ ID NO:1), At4g16110 (ARR2) (SEQ ID NO:3), and At2g25180 (ARR12) (SEQ ID NO: 5). The obtained PCR products were each cloned into pMD20T to construct pMD20T-ARR1, pMD20T-ARR2, and pMD20T-ARR12. The inserted PCR products were sequenced to confirm that no mutation was introduced.

(Construction of Transcription Factor Expression Vector)

The plasmids constructed in (Acquisition of transcription factor gene) were restricted with SpeI, BamHI, or EcoRV, and the transcription factor genes were individually incorporated downstream of the TEF1 promoter region of p427TEF (COSMO BIO Co., Ltd.) to construct pTEF-ARR1, pTEF-ARR2, and pTEF-ARR12. Ligation high ver. 2 was used for ligation.

(Transformation of Yeast)

The plasmids constructed in (Construction of vector for gene introduction into yeast chromosome) and (Construction of transcription factor expression vector) were introduced into yeast cells (BY4741 strain) by electroporation. Screening for transgenic yeast cells was carried out by culturing the yeast cells on a medium containing the antifungal antibiotics Aureobasidin A (Takara Bio, Inc.) and G418 (Wako Pure Chemical Industries, Ltd.).

(Demonstration of Effect of Transcription Factor)

The transgenic yeast cells were cultured on a medium containing X-gal to assess the expression of lacZ due to transcription factor activity. Specifically, when the lacZ reporter gene, which is linked to each promoter sequence, is expressed, X-gal in the medium is then decomposed to develop a blue color. Based on this mechanism, when the medium turned blue, it was determined that lacZ was expressed due to transcription factor activity. This test was repeated 10 times. Table 1 shows how many times lacZ was expressed due to transcription factor activity.

TABLE 1

| | Transcription factor | | | |
|---|---|---|---|---|
| Promoter sequence | At3g16857 (ARR1) | At4g16110 (ARR2) | At2g25180 (ARR12) | Control (No transcription factor) |
| hmg(−1500) | 5 | 3 | 3 | 1 |
| hmg(−1000) | 2 | 2 | 1 | 1 |
| hmg(−500) | 2 | 1 | 0 | 0 |
| ipp(−1000) | 7 | 6 | 4 | 0 |
| ipp(−500) | 5 | 4 | 2 | 0 |
| cpt(−500) | 2 | 1 | 1 | 0 |
| srpp(−1000) | 8 | 6 | 4 | 2 |
| srpp(−500) | 5 | 4 | 2 | 1 |

Number of yeast cells that exhibited reporter gene activity (N = 10)

Table 1 shows that the use of At3g16857 (ARR1) (SEQ ID NOs:1 and 2), At4g16110 (ARR2) (SEQ ID NOs:3 and 4), or At2g25180 (ARR12) (SEQ ID NOs:5 and 6), particularly At3g16857 (ARR1), enhanced the reporter gene activity. Further, At3g16857 (ARR1), At4g16110 (ARR2), and At2g25180 (ARR12) have proved to function as transcription factors for HMG-CoA reductase, IPP isomerase, cis-prenyltransferase, and small rubber particle protein because the longer the sequence of the promoter region was, the more often the reporter gene activity was expressed, or, in other words, the larger number of At3g16857 (ARR1), At4g16110 (ARR2), or At2g25180 (ARR12)-binding sites the promoter sequence contained, the more often the reporter gene activity was expressed. These results demonstrated that by introducing At3g16857 (ARR1), At4g16110 (ARR2), or At2g25180 (ARR12), particularly At3g16857 (ARR1), into an isoprenoid-producing plant, the overall pathway of polyisoprenoid biosynthesis can be enhanced to increase polyisoprenoid production.

(Sequence Listing Free Text)

SEQ ID NO:1: base sequence of ARR1-encoding gene from *Arabidopsis thaliana*
SEQ ID NO:2: amino acid sequence of ARR1 from *Arabidopsis thaliana*
SEQ ID NO:3: base sequence of ARR2-encoding gene from *Arabidopsis thaliana*
SEQ ID NO:4: amino acid sequence of ARR2 from *Arabidopsis thaliana*
SEQ ID NO:5: base sequence of ARR12-encoding gene from *Arabidopsis thaliana*
SEQ ID NO:6: amino acid sequence of ARR12 from *Arabidopsis thaliana*
SEQ ID NO:7: base sequence of cis-prenyltransferase-encoding gene from *Hevea brasiliensis*
SEQ ID NO:8: amino acid sequence of cis-prenyltransferase from *Hevea brasiliensis*
SEQ ID NO:9: base sequence of HMG-CoA reductase-encoding gene from *Hevea brasiliensis*
SEQ ID NO:10: amino acid sequence of HMG-CoA reductase from *Hevea brasiliensis*
SEQ ID NO:11: base sequence of IPP isomerase-encoding gene from *Hevea brasiliensis*
SEQ ID NO:12: amino acid sequence of IPP isomerase from *Hevea brasiliensis*
SEQ ID NO:13: base sequence of SRPP-encoding gene from *Hevea brasiliensis*
SEQ ID NO:14: amino acid sequence of SRPP from *Hevea brasiliensis*
SEQ ID NO:15: Primer 1
SEQ ID NO:16: Primer 2
SEQ ID NO:17: Primer 3
SEQ ID NO:18: Primer 4
SEQ ID NO:19: Primer 5
SEQ ID NO:20: Primer 6
SEQ ID NO:21: base sequence of promoter sequence of HMG-CoA reductase from *Hevea brasiliensis*
SEQ ID NO:22: base sequence of promoter sequence of IPP isomerase from *Hevea brasiliensis*
SEQ ID NO:23: base sequence of promoter sequence of cis-prenyltransferase from *Hevea brasiliensis*
SEQ ID NO:24: base sequence of promoter sequence of SRPP from *Hevea brasiliensis*

The invention claimed is:

1. A *Hevea* plant, into which an expression vector comprising a heterologous gene encoding a cytokinin-responsive transcription factor has been introduced,
   wherein the gene is either of the following DNAs:
   [1] a DNA comprising the sequence of SEQ ID NO: 3; and
   [2] a DNA encoding a protein with transcription factor activity having a sequence that has at least 95% sequence identity to the sequence of SEQ ID NO: 3,
   wherein the introduced gene increases polyisoprenoid production in the plant.

2. A method of producing a polyisoprenoid, said method comprising:
   growing the isoprenoid-producing plant of claim 1.

* * * * *